US010034857B2

(12) United States Patent
Lipp

(10) Patent No.: US 10,034,857 B2
(45) Date of Patent: Jul. 31, 2018

(54) TRIPTAN POWDERS FOR PULMONARY DELIVERY

(71) Applicant: Civitas Therapeutics, Inc., Chelsea, MA (US)

(72) Inventor: Michael M. Lipp, Framingham, MA (US)

(73) Assignee: Civitas Therapeutics, Inc., Chelsea, MA (US)

( * ) Notice: Subject to any disclaimer, the term of this patent is extended or adjusted under 35 U.S.C. 154(b) by 0 days.

(21) Appl. No.: 15/200,335

(22) Filed: Jul. 1, 2016

(65) Prior Publication Data

US 2017/0000765 A1  Jan. 5, 2017

Related U.S. Application Data

(60) Provisional application No. 62/188,338, filed on Jul. 2, 2015.

(51) Int. Cl.
*A61K 31/405* (2006.01)
*A61K 31/4045* (2006.01)
*A61K 9/16* (2006.01)
*A61K 9/00* (2006.01)

(52) U.S. Cl.
CPC ........ *A61K 31/4045* (2013.01); *A61K 9/0075* (2013.01); *A61K 9/1611* (2013.01); *A61K 9/1617* (2013.01); *A61K 9/1623* (2013.01); *A61K 9/1652* (2013.01)

(58) Field of Classification Search
CPC .................................................... C07D 209/08
USPC ........................................................ 514/415
See application file for complete search history.

(56) References Cited

U.S. PATENT DOCUMENTS

| 4,636,521 | A | 1/1987 | Coates et al. |
|---|---|---|---|
| 5,855,913 | A | 1/1999 | Hanes et al. |
| 5,874,064 | A | 2/1999 | Edwards et al. |
| 5,985,309 | A | 11/1999 | Edwards et al. |
| RE37,053 | E | 2/2001 | Hanes et al. |
| 6,254,854 | B1 | 7/2001 | Edwards et al. |
| 6,383,471 | B1 | 5/2002 | Chen et al. |
| 6,461,591 | B1 | 10/2002 | Keller et al. |
| 6,503,480 | B1 | 1/2003 | Edwards et al. |
| 6,514,482 | B1 | 2/2003 | Bartus et al. |
| 6,569,463 | B2 | 5/2003 | Patel et al. |
| 6,585,958 | B1 | 7/2003 | Keller et al. |
| 6,604,698 | B2 | 8/2003 | Verhoff et al. |
| 6,613,308 | B2 | 9/2003 | Bartus et al. |
| 6,645,528 | B1 | 11/2003 | Straub et al. |
| 6,652,837 | B1 | 11/2003 | Edwards et al. |
| 6,682,716 | B2 | 1/2004 | Hodges et al. |
| 6,732,732 | B2 | 5/2004 | Edwards et al. |
| 6,740,309 | B2 | 5/2004 | Rabinowitz et al. |
| 6,743,415 | B2 | 6/2004 | Rabinowitz et al. |
| 6,759,029 | B2 | 7/2004 | Hale et al. |
| 6,848,197 | B2 | 2/2005 | Chen et al. |
| 6,858,199 | B1 | 2/2005 | Edwards et al. |
| 6,923,988 | B2 | 8/2005 | Patel et al. |
| 6,977,087 | B2 | 12/2005 | Edwards et al. |
| 6,979,437 | B2 | 12/2005 | Bartus et al. |
| 7,005,121 | B2 | 2/2006 | Rabinowitz et al. |
| 7,008,644 | B2 | 3/2006 | Batycky et al. |
| 7,011,819 | B2 | 3/2006 | Hale et al. |
| 7,018,621 | B2 | 3/2006 | Hale et al. |
| 7,045,118 | B2 | 5/2006 | Rabinowitz et al. |
| 7,048,908 | B2 | 5/2006 | Basu et al. |
| 7,052,678 | B2 | 5/2006 | Vanbever et al. |
| 7,090,830 | B2 | 8/2006 | Hale et al. |
| 7,146,978 | B2 | 12/2006 | Edwards et al. |
| 7,182,961 | B2 | 2/2007 | Batycky et al. |
| 7,189,753 | B1 | 3/2007 | Cady et al. |
| 7,252,840 | B1 | 8/2007 | Batycky et al. |
| 7,384,649 | B2 | 6/2008 | Batycky et al. |
| 7,498,019 | B2 | 3/2009 | Hale et al. |
| 7,556,798 | B2 | 7/2009 | Edwards et al. |
| 7,582,284 | B2 | 9/2009 | Kordikowski et al. |
| 7,628,977 | B2 | 12/2009 | Edwards et al. |
| 7,754,242 | B2 | 7/2010 | Basu et al. |
| 7,799,337 | B2 | 9/2010 | Levin |
| 7,947,742 | B2 | 5/2011 | Batycky et al. |
| 7,954,491 | B2 | 6/2011 | Hrkach |
| 8,096,968 | B2 | 1/2012 | Rasor et al. |
| 8,268,791 | B2 | 9/2012 | Maggio |
| RE43,711 | E | 10/2012 | Jackson et al. |
| 8,337,817 | B2 | 12/2012 | Nagata et al. |
| 8,415,397 | B2 | 4/2013 | Batycky et al. |
| 8,440,631 | B2 | 5/2013 | Maggio |
| 8,496,002 | B2 | 7/2013 | Ellwanger et al. |
| 8,614,255 | B2 | 12/2013 | Blizzard et al. |
| 8,673,360 | B2 | 3/2014 | Nagata et al. |
| 2004/0005275 | A1 | 1/2004 | Gizurarson et al. |
| 2004/0025876 | A1 | 2/2004 | Miller et al. |
| 2004/0162333 | A1 | 8/2004 | Mezaache et al. |
| 2005/0261278 | A1 | 11/2005 | Weiner et al. |
| 2006/0120962 | A1 | 6/2006 | Rabinowitz et al. |
| 2006/0172017 | A1 | 8/2006 | Rasor et al. |
| 2007/0178166 | A1 | 8/2007 | Bernstein et al. |
| 2008/0066739 | A1 | 3/2008 | LeMahieu et al. |

(Continued)

FOREIGN PATENT DOCUMENTS

| EP | 0496307 A1 | 7/1992 |
|---|---|---|
| EP | 1598066 A1 | 11/2005 |

(Continued)

OTHER PUBLICATIONS

U.S. Appl. No. 15/143,131, filed Apr. 29, 2016.

(Continued)

*Primary Examiner* — Raymond J Henley, III
(74) *Attorney, Agent, or Firm* — Elmore Patent Law Group, P.C.; Edgar W. Harlan; Carolyn S. Elmore

(57) ABSTRACT

The invention provides stable, spray-dried, particle formulations containing a triptan, preferably sumatriptan, or a pharmaceutically acceptable salt thereof, which are useful for pulmonary administration to the respiratory tract of a patient for the treatment of disease.

22 Claims, No Drawings

(56) References Cited

U.S. PATENT DOCUMENTS

| | | |
|---|---|---|
| 2008/0078382 A1 | 4/2008 | LeMahieu et al. |
| 2008/0299048 A1 | 12/2008 | Hale et al. |
| 2008/0317863 A1 | 12/2008 | Nystrom et al. |
| 2009/0163451 A1 | 6/2009 | Porreca et al. |
| 2009/0220611 A1 | 9/2009 | Dargelas et al. |
| 2009/0232898 A1 | 9/2009 | Pettersson et al. |
| 2010/0008995 A1 | 1/2010 | Duncalf et al. |
| 2010/0065048 A1 | 3/2010 | Mueller-Walz et al. |
| 2010/0288275 A1 | 11/2010 | Djupesland et al. |
| 2010/0316724 A1 | 12/2010 | Whitfield et al. |
| 2011/0021583 A1 | 1/2011 | Holl et al. |
| 2011/0077272 A1 | 3/2011 | Main |
| 2011/0112157 A1 | 5/2011 | Datta et al. |
| 2011/0118189 A1 | 5/2011 | Farr et al. |
| 2011/0120456 A1 | 5/2011 | Immel |
| 2011/0142914 A1 | 6/2011 | Persaud et al. |
| 2012/0132204 A1 | 5/2012 | Lucking et al. |
| 2013/0116215 A1 | 5/2013 | Coma et al. |
| 2013/0253009 A1 | 9/2013 | Maggio |
| 2014/0007874 A1 | 1/2014 | Ellwanger et al. |
| 2014/0193501 A1 | 7/2014 | Bartus et al. |
| 2014/0220119 A1 | 8/2014 | Kee et al. |

FOREIGN PATENT DOCUMENTS

| | | |
|---|---|---|
| WO | 2002083220 A2 | 10/2002 |
| WO | 200380163 A1 | 10/2003 |
| WO | 2003079885 A2 | 10/2003 |
| WO | 2003079992 A2 | 10/2003 |
| WO | 2004002551 A2 | 1/2004 |
| WO | 2004112702 A2 | 12/2004 |
| WO | 2008156586 A2 | 12/2008 |
| WO | 2009026434 A1 | 2/2009 |
| WO | 2009095684 A1 | 8/2009 |
| WO | 2012064892 A1 | 5/2012 |
| WO | 2013128447 A1 | 9/2013 |
| WO | 2014078258 A1 | 5/2014 |

OTHER PUBLICATIONS

Rabinowitz, J.D., "Fast Onset Medications through Thermally Generated Aerosols." The Journal of Pharmacology and Experimental Therapeutics, vol. 309(2): pp. 769-775, 2004.

Yang, Z., et al., "Production of Ultrafine Sumatriptan Succinate Particles for Pulmonary Delivery," Pharmaceutical Research, vol. 25(9), pp. 2012-2018, 2008.

TRIPTAN POWDERS FOR PULMONARY DELIVERY

RELATED APPLICATION

This application claims the benefit of U.S. Provisional Application No. 62/188,338, filed on Jul. 2, 2015. The entire teachings of the above application are incorporated herein by reference.

BACKGROUND OF THE INVENTION

Sumatriptan, which has the structure below, is a drug used in the treatment of migraine.

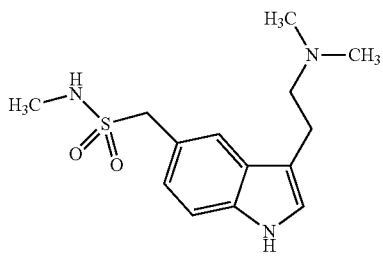

Sumatriptan is available in the form of tablets for oral administration, solution for injection and solution for nasal spray.

SUMMARY OF THE INVENTION

The invention provides stable, spray-dried, particle formulations containing a triptan, such as sumatriptan, or a pharmaceutically acceptable salt of thereof, which are useful for pulmonary administration to the respiratory tract for treating migraine.

DETAILED DESCRIPTION OF THE INVENTION

In one embodiment, the invention is a stable, pharmaceutical composition of a triptan or a pharmaceutically acceptable salt thereof formulated for pulmonary delivery comprising spray-dried particles (also referred to herein as "powders" or "dry powders") comprising the triptan or pharmaceutically acceptable salt thereof, wherein the triptan or salt thereof is present in the particles in amorphous form, crystalline form, or in a combination of both amorphous and crystalline forms.

Examples of triptans which can be formulated according to the invention included sumatriptan, zolmitriptan, rizatriptan, naratriptan, eletriptan, almortriptan, frovatriptan and avitriptan. In one embodiment, the triptan is not zolmitriptan. In preferred embodiments, the triptan is sumatriptan. A preferred sumatriptan salt is sumatriptan succinate.

In one embodiment, the invention is a pharmaceutical composition of a triptan, or a pharmaceutically acceptable salt thereof for pulmonary delivery comprising spray-dried particles containing the triptan or a pharmaceutically acceptable salt thereof and having a tap density of less than about 0.2 g/cm$^3$. In one aspect of the invention, the tap density is from about 0.02 to 0.20 g/cm$^3$. In another aspect of the invention, the tap density is from about 0.02 to 0.175 g/cm$^3$. In a further aspect of the invention, the tap density is from about 0.03 to 0.175 g/cm$^3$. In a further aspect of the invention, the tap density is from about 0.06 to 0.175 g/cm$^3$. In one aspect of the invention, the tap density is from about 0.03 to 0.15 g/cm$^3$. In another aspect of the invention the volume mean geometric diameter is about 3 μm to 20 μm, 5 μm to 20 μm, 5 μm to 10 μm, 7 μm to 15 μm, or 7 μm to 10 μm.

In one embodiment, the invention is a pharmaceutical composition for pulmonary delivery comprising particles containing a triptan or a pharmaceutically acceptable salt thereof and having a volume mean geometric diameter of greater than about 5 microns (μm) and a tap density of less than about 0.20 g/cm$^3$.

In another embodiment, the invention is a method of delivering a triptan to the pulmonary system of a patient comprising the steps of: providing a spray-dried particle formulation of the triptan or a pharmaceutically acceptable salt thereof in a compartment and an inhaler to a patient wherein said powder comprises particles of the triptan or a pharmaceutically acceptable salt thereof; dispersing the powder by breath actuation of the patient; and delivering the particles to the patient's respiratory system.

In one aspect of this invention, an inhaler is a dry powder inhaler. A variety of inhalers can be used including the Aerolizer, Diskus, Flexhaler, Handihaler, Neohaler, Pressair, Rotahaler, Turbohaler, and Twisthaler. Other dry powder inhalers which can be used are described in U.S. Pat. No. 6,766,799, U.S. Pat. No. 7,278,425 and U.S. Pat. No. 8,496,002 each of which are hereby incorporated in by reference for their disclosure relating to the inhalation devices described therein. In one aspect of the invention, the compartment is a capsule or a blister pack. In one aspect of the invention, the inhaler has a resistance of about 0.05 to about 0.25, about 0.15 to about 0.25, 0.05 to about 0.15, 0.2 to about 0.25, or about 0.2. Resistance as referred herein is measured in: Square root of $Cm_{H2O}$/Liters per minute.

In another aspect of the invention, the triptan powder in said compartment has a volume median geometric diameter of greater than about 3 μm, of about 3 μm to about 30 μm, of about 3 μm to about 20 μm, of about 5 μm to about 20 μm, of about 5 μm to about 15 μm, of about 5 μm to about 10 μm, or of about 7 μm to about 10 μm. In one specific embodiment, the particles in said compartment have a volume median geometric diameter of 6-10 μm and the particles delivered to the patient's respiratory tract have a volume median geometric diameter of 8-9 μm. In another embodiment, the particles delivered to the patient's respiratory tract have a volume median geometric diameter of 6-8 μm. In another embodiment, the particles delivered to the patient's respiratory tract have a 5 to 20% smaller, 5 to 10% smaller, or 8 to 15% smaller volume median geometric diameter than the particles in said compartment.

In one embodiment, the invention is a pharmaceutical composition for pulmonary delivery comprising particles comprising a triptan or a pharmaceutically acceptable salt thereof having a volume median geometric diameter of greater than about 5 μm and a tap density of less than about 0.20 g/cm$^3$.

In one embodiment, the particles comprise the triptan or a pharmaceutically acceptable salt thereof, a phospholipid and a salt. In another aspect of this invention, the particles comprise the triptan or a pharmaceutically acceptable salt thereof, a phospholipid, a salt, an optional amino acid, and an optional sugar and/or sugar alcohol.

Examples of salts suitable for use in the compositions of the invention include, but are not limited to sodium chloride (NaCl), sodium citrate, sodium lactate, and potassium chloride. Examples of phospholipids suitable for use in the compositions of the invention include, but are not limited to, dipalmitoylphosphatidylcholine (DPPC) dilauroylphosphatidylcholine (DLPC), disaturated-phosphatidylcholine (DSPC). In one embodiment, the sodium chloride is present in 1%, 2%, or 3% by weight. Examples of amino acids suitable for use in the compositions of the invention include, but are not limited to, hydrophobic amino acids such as leucine, isoleucine, alanine, valine, phenylalanine and glycine. In one embodiment, the chiral amino acid is an L-amino acid, and the term leucine as used herein refers to L-leucine unless otherwise indicated. Examples of sugars and sugar alcohols suitable for use in the compositions of the invention include, but are not limited to, lactose, trehalose, mannitol, maltodextrin and polyglycitol. The maltodextrin can have a dextrose equivalence (DE) of 3 to 20%. In certain embodiments, the maltodextrin has a DE of 4-7%, 10-12% or 16-19%. In one embodiment, the maltodextrin has a DE of 10.7%. In certain embodiments, the polyglycitol is SD-30 or SD-60.

In one embodiment, the particles comprise sumatriptan or a pharmaceutically acceptable salt thereof, DPPC, sodium chloride and maltodextrin.

In one embodiment, the particles comprise sumatriptan or a pharmaceutically acceptable salt thereof, DPPC, sodium chloride and 1-leucine.

In one embodiment, the pharmaceutical composition contains a powder comprising 5 to 50% triptan or a pharmaceutically acceptable salt thereof, 5-20% phospholipid, and 1-10% sodium chloride as measured by percent of dry solids in the powder. In preferred embodiments, the pharmaceutical composition contains a powder comprising 25 to 55% or 30 to 50% triptan or a pharmaceutically acceptable salt thereof, 5-20% phospholipid, 1-10% sodium chloride and 25 to 60% or 30 to 50% of an excipient selected from maltodextrins, lactose, glycine, trehalose, mannitol and 1-leucine, as measured by percent of dry solids in the powder. In one embodiment, the tritan is sumatriptan free base. In another embodiment the triptan is a sumatriptan salt, such as sumatriptan succinate salt.

In one embodiment, the pharmaceutical composition contains a powder comprising 25 to 55% or 30 to 50% triptan or a pharmaceutically acceptable salt thereof, preferably sumatriptan free base, 15-20% phospholipid, 1-5% sodium chloride and 25 to 55% or 30 to 50% of an excipient selected from maltodextrins, and 1-leucine, as measured by percent of dry solids in the powder. In a preferred embodiment, the powder comprises 30 to 50% triptan or a pharmaceutically acceptable salt thereof, preferably sumatriptan free base, about 18% phospholipid, such as DPPC, about 2% sodium chloride and 30 to 50% of an excipient selected from maltodextrins, such as polyglycitol (for example, SD-30 or SD-60) or maltodextrin (DE=10.7%), as measured by percent of dry solids in the powder.

In one embodiment the triptan is sumatriptan (free base or succinate salt) and the pharmaceutical composition has a formulation shown in Table 1 or Table 2, where the amount of each component is provided as weight %.

TABLE 1

| Sumatriptan Succinate | DPPC | Sodium Chloride | Amino Acid | Sugar/Sugar alcohol |
|---|---|---|---|---|
| 25% | 18% | 2% | 55% (leucine) | 0 |
| 50% | 18% | 2% | 30% (leucine) | 0 |
| 50% | 18% | 2% | 0 | 30% (maltodextrin; DE = 4.0-7.0%, 10.7%, 16.0-19.0%) |

TABLE 1-continued

| Sumatriptan Succinate | DPPC | Sodium Chloride | Amino Acid | Sugar/Sugar alcohol |
|---|---|---|---|---|
| 50% | 18% | 2% | 0 | 30% (lactose) |
| 50% | 18% | 2% | 0 | 30% (mannitol) |
| 50% | 18% | 2% | 0 | 30% (trehalose) |
| 25% | 18% | 2% | 0 | 55% (trehalose) |

TABLE 2

| Sumatriptan Free base | DPPC | Sodium Chloride | Amino Acid | Sugar/Sugar alcohol |
|---|---|---|---|---|
| 50% | 18% | 2% | 30% (leucine) | 0 |
| 50% | 18% | 2% | 0 | 30% (maltodextrin; DE = 4.0-7.0%, 10.7%, 16.0-19.0%) |
| 50% | 18% | 2% | 0 | 30% (lactose) |
| 50% | 18% | 2% | 30% (glycine) | 0 |

In one embodiment, particles of this invention have an external surface area of greater than 10 $m^2/g$. In another embodiment, the external surface area is greater than 15 $m^2/g$, greater than 20 $m^2/g$ or about 10 to about 50 $m^2/g$.

Gravimetric analysis, using Cascade impactors, is a method of measuring the size distribution of airborne particles. The Andersen Cascade Impactor (ACI) is an eight-stage impactor that can separate aerosols into nine distinct fractions based on aerodynamic size. The size cutoffs of each stage are dependent upon the flow rate at which the ACI is operated. Preferably the ACI is calibrated at 60 L/min. In one embodiment, a two-stage collapsed ACI is used for particle optimization. The two-stage collapsed ACI consists of stages 0, 2 and F of the eight-stage ACI and allows for the collection of two separate powder fractions. At each stage an aerosol stream passes through the nozzles and impinges upon the surface. Particles in the aerosol stream with a large enough inertia will impact upon the plate. Smaller particles that do not have enough inertia to impact on the plate will remain in the aerosol stream and be carried to the next stage.

The ACI is calibrated so that the fraction of powder that is collected on a first stage is referred to herein as "fine particle fraction" or "FPF". The FPF corresponds to the percentage of particles that have an aerodynamic diameter of less than 5.6 μm. The fraction of powder that passed the first stage of the ACI and is deposited on the collection filter is referred to as "FPF(3.4)". This corresponds to the percentage of particles having an aerodynamic diameter of less than 3.4 μm.

The FPF fraction has been demonstrated to correlate to the fraction of the powder that is deposited in the lungs of the patient, while the FPF(3.4) has been demonstrated to correlate to the fraction of the powder that reaches the deep lung of a patient.

In accordance with the invention, the FPF of the inhalable powder of the nominal dose contained in the capsule (i.e., the percentage of particles in the powder contained in the capsule that have an aerodynamic diameter of less than 5.6 μm) is about 20%, 30%, 40% or more. In one embodiment the FPF of the nominal dose of the inhalable powder contained in the capsule is about 50%, 60%, or 70%. In one embodiment the FPF is about 30% to about 90% of the nominal dose of the inhalable powder contained in the inhaler. In one embodiment the FPF is about 50% to about 60% of the nominal dose of the inhalable powder contained in the inhaler. In one embodiment the FPF is about 40% to about 60% of the nominal dose of the inhalable powder contained in the inhaler. In one embodiment the FPF is about 50% to about 56% of the nominal dose of the inhalable powder contained in the inhaler. In one embodiment the FPF is about 30% to about 60% of the nominal dose of the inhalable powder contained in the inhaler. In one embodiment the FPF is about 45%, 46%, 47%, 48%, 49%, 50%, 51%, 52%, 53%, 54%, 55%, 56%, 57%, 58%, 59%, or 60% of the nominal dose of the inhalable powder contained in the inhaler.

In accordance with the invention, the FPF(3.4) of the inhalable powder of the nominal dose contained in the capsule (i.e., the percentage of particles in the powder contained in the capsule that have an aerodynamic diameter of less than 3.4 µm) is about 30%, 40%, 50% or more. In one embodiment the FPF(3.4) of the nominal dose of the inhalable powder contained in the capsule is about 30% or more. In one embodiment the FPF(3.4) is at least about 40% or 50% of the nominal dose of the inhalable powder contained in the inhaler. In one embodiment the FPF(3.4) is about 30% to 60% of the nominal dose of the inhalable powder contained in the inhaler. In one embodiment the FPF(3.4) is about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% of the nominal dose of the inhalable powder contained in the inhaler.

As used herein, the term "nominal powder dose" is the total amount of powder held in the capsule. As used herein, the term "nominal drug dose" is the total amount of triptan or triptan salt contained in the nominal powder dose. The nominal powder dose is related to the nominal drug dose by the load percent of drug in the powder.

In one embodiment, the nominal powder dose is 25-50 mg by dry weight. In a further embodiment, the nominal powder dose is 25-40 mg by dry weight. In a still further embodiment, the nominal powder dose is 30-35 mg by dry weight or 32-38 mg by dry weight.

Another method for measuring the size distribution of airborne particles is the Multi-stage liquid Impinger (MSLI). The Multi-stage liquid Impinger (MSLI) operates on the same principles as the Anderson Cascade Impactor (ACI), but instead of eight stages there are five in the MSLI. Additionally, instead of each stage consisting of a solid plate, each MSLI stage consists of a methanol-wetted glass frit. The wetted stage is used to prevent bouncing and re-entrainment, which can occur using the ACI. The MSLI is used to provide an indication of the flow rate dependence of the powder. This can be accomplished by operating the MSLI at 30, 60, and 90 L/min and measuring the fraction of the powder collected on stage 1 and the collection filter. If the fractions on each stage remain relatively constant across the different flow rates, then the powder is considered to be approaching flow rate independence.

In one embodiment, the inhalable powders of the invention have a tap density of less than about 0.075 g/cm$^3$. For example, the particles have a tap density between 0.02 and 0.20 g/cm$^3$, between 0.02 and 0.15 g/cm$^3$, between 0.03 and 0.12 g/cm$^3$, between 0.05 and 0.15 g/cm$^3$, or less than about 0.15 g/cm$^3$, or a tap density less than about 0.10 g/cm$^3$, or a tap density less than about 0.15 g/cm$^3$, or between 0.06 to 0.15 g/cm$^3$. Tap density can be measured by using instruments known to those skilled in the art such as the Dual Platform Microprocessor Controlled Tap Density Tester (Vankel, N.C.) or a GEOPYC™ instrument (Micrometrics Instrument Corp., Norcross, Ga., 30093). Tap density is a standard measure of the envelope mass density. Tap density can be determined using the method of USP Bulk Density and Tapped Density, United States Pharmacopeia convention, Rockville, Md., 10th Supplement, 4950-4951, 1999. Features which can contribute to low tap density include irregular surface texture and porous structure. The envelope mass density of an isotropic particle is defined as the mass of the particle divided by the minimum sphere envelope volume within which it can be enclosed. In one embodiment of the invention, the particles have an envelope mass density of less than about 0.4 g/cm$^3$.

The inhalable powder of the invention has a preferred particle size, e.g., a volume mean geometric diameter (VMGD) of at least about 1 micron (µm). In embodiments, the VMGD is greater than 3 µm or greater than 5 µm. In other embodiments, the VMGD is between about 5 µm and 20 µm, between about 5 µm and 10 µm, between about 6 µm and 15 µm and between about 7 µm and 12 µm. In another aspect of the invention, the powder particles have a VMGD of about 2 µm to 15 µm, 3 µm to 12 µm, 3 µm to 8 µm, 5 µm to 9 µm, or 6 µm to 9 µm. The diameter of the spray-dried particles, for example, the VMGD, can be measured using a laser diffraction instrument (for example Helos, manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition to targeted sites within the respiratory tract.

The particles of the inhalable powder of the invention preferably have a "mass median aerodynamic diameter" (MMAD), also referred to herein as "aerodynamic diameter", between about 1 µm and about 5 µm or any subrange encompassed between about 1 µm and about 5 µm. For example, but not limited to, the MMAD is between about 1 µm and about 3 µm, or the MMAD is between about 3 µm and about 5 µm. In one embodiment, the MMAD is between 1.5 µm and 2.5 µm. Experimentally, aerodynamic diameter can be determined by employing a gravitational settling method, whereby the time for an ensemble of powder particles to settle a certain distance is used to infer directly the aerodynamic diameter of the particles. An indirect method for measuring the mass median aerodynamic diameter (MMAD) is the multi-stage liquid impinger (MSLI). The aerodynamic diameter, $d_{aer}$, can be calculated from the equation:

$$d_{aer}=d_g\sqrt{\rho_{tap}}$$

where $d_g$ is the geometric diameter, for example the MMGD, and ρ is the powder density.

Powders for use in capsules of this invention are typically produced by spray drying. In some cases, spray-drying can produce extremely dry particles which may have poor handling properties and may be difficult to compact into a capsule in a dense manner. A nitrogen source with a specified moisture level may be blown over, across, or through the dry powder to add a specific moisture content to the dry powder. Such moisture can provide the desired working density of the powder. Moisture content can be about 1-10% by weight, about 1-5% by weight, or 2-3% by weight. Spray drying methods in accordance with the invention are described in the Examples herein and in U.S. Pat. Nos. 6,848,197 and 8,197,845, incorporated herein by reference.

In certain embodiments, the triptan particles of the invention are prepared by the following process. DPPC, and the triptan salt or free base are allowed to equilibrate to room temperature before weighing. Required amounts of water and ethanol are transferred to the aqueous and organic phase feed vessels respectively, and then stirred. In embodiments in which the triptan is sumatriptan in the form of the succinate salt, the required amounts of sodium chloride, the excipient of choice (for example, L-leucine, glycine, maltodextrin, mannitol, or trehalose) and sumatriptan succinate are dissolved in the aqueous phase vessel. The required amount of DPPC is dissolved in the organic phase vessel.

In embodiments in which the triptan is sumatriptan free base, the required amounts of sodium chloride and the excipient of choice (for example, L-leucine, glycine, maltodextrin, mannitol, or trehalose) are dissolved in the aqueous phase vessel. The required amount of sumatriptan free base and DPPC are dissolved in the organic phase vessel.

Spray drying is initiated by starting the drying gas flow and heating up the drying gas by setting the desired inlet temperature. After the spray dryer outlet temperature reaches a suitable temperature, for example 55° C., the liquid skid inlet is set to allow blank solvents to be atomized with the aid of nitrogen into the spray dryer, and the system is allowed to cool and stabilize, for example, at a temperature of 40 to 50° C., preferably 44° C. Product filter pulsing is initiated and product filter purge flow is set to 10 to 20 scfh, preferably about 15 scfh. After the system stabilizes, the liquid skid inlet is switched to the feed solvents prepared above and the process is continued till the feed solvents run out. At the point when feed solvents run out, the liquid skid inlet is switched back to blank solvents which are allowed to spray for about 5 to 20 minutes. At this point, powder collected at the bottom of the product filter is transferred to its final collection vessel in a glove box maintained at a relative humidity of about 10 to 20%, preferably about 15%. After spraying the blank solvent for 5 to 20 minutes, preferably about 10 minutes, the system is shut down by shutting down the liquid lines, atomization gas, drying gas heater, drying gas inlet and finally the exhaust.

The inhalable powder comprising a triptan as described above is used to fill capsules suitable for use in an inhaler. The term "capsule material" as used herein refers to the material from which the shell of the capsule for inhalation is made. In one embodiment, the capsule material according to the invention is selected from among gelatin, cellulose derivatives, starch, starch derivatives, chitosan and synthetic plastics.

If gelatin is used as the capsule material, examples according to the invention may be selected from among polyethyleneglycol (PEG), PEG 3350, glycerol, sorbitol, propyleneglycol, PEO-PPO block copolymers and other polyalcohols and polyethers. If cellulose derivatives are used as the capsule material, examples according to the invention may be selected from hydroxypropylmethylcellulose (HPMC), hydroxypropylcellulose, methylcellulose, hydroxymethylcellulose and hydroxyethylcellulose. If synthetic plastics are used as the capsule material, examples according to the invention may be selected from polyethylene, polycarbonate, polyester, polypropylene and polyethylene terephthalate. In one embodiment, the capsule material further comprises titanium dioxide. In one preferred embodiment the capsule comprises HPMC and titanium dioxide. In one embodiment, the capsule comprises carrageenan. In a further embodiment, the capsule comprises potassium chloride. In a still further embodiment, the capsule comprises, HPMC, carrageenan, potassium chloride, and titanium dioxide. In one embodiment, the capsule size is selected from 000, 00, 0, 1, or 2. In a specific embodiment, the capsule size is 00. In another specific embodiment, the capsule size is 2.

In one specific embodiment, the capsule is a hydroxypropylmethylcellulose (HPMC) capsule. In another specific embodiment, the capsule is a hydroxypropylmethylcellulose size 00 capsule. In one specific embodiment the capsule material comprises HPMC and titanium dioxide and the capsule size is 00.

In one embodiment, a 00 capsule contains between 15 and 50 mg of sumatriptan by dry weight. In another embodiment, a 00 capsule contains between 20 and 40 mg of sumatriptan by dry weight. In another embodiment, a 00 capsule contains between 25 and 35 mg of sumatriptan by dry weight. In another embodiment, a 00 capsule contains about 30, 31, 32, 33, 34, 35, 36, 37, 38, 39, or 40 mg of sumatriptan by dry weight.

In one aspect of the invention, the powders have low electrostatic charge to enable high dispersion from the capsule.

The capsules of the invention are particularly suitable for use in a dry powder inhaler for the delivery of a dry powder composition comprising an effective amount of a triptan, preferably sumatriptan or salt thereof, to a subject in need thereof, for example, for treating migraine or cluster headache.

In one embodiment, the invention provides a method for treating migraine in a subject in need thereof, preferably a human patient, comprising the step of administering to the subject a therapeutically effective amount of a triptan composition of the invention. The composition is preferably administered to the subject's pulmonary system, for example, using an inhaler, such as a dry powder inhaler, as described herein. The triptan compositions of the invention are useful for the acute treatment of migraine, providing relief of one or more symptoms of migraine, for example, pain, nausea, photophobia or phonophobia. and/or shortening the duration of migraine. In certain embodiments, administration of a triptan composition of the invention provides relief of pain. In certain embodiments, administration of a triptan composition of the invention provides relief of pain and at least one of nausea, photophobia and phonophobia. In certain embodiments, administration of a triptan composition of the invention provides relief of at least pain and nausea. In certain embodiments, administration of a triptan composition of the invention provides relief of each of pain, nausea, photophobia and phonophobia. The migraine to be treated can be migraine with or without aura. In preferred embodiments, administration of the triptan formulation of the invention provides relief of pain within about 15 minutes or within about 30 minutes of administration.

In another embodiment, the invention provides a method for treating cluster headache in a subject in need thereof, preferably a human patient, comprising the step of administering to the subject a therapeutically effective amount of a triptan composition of the invention. The triptan compositions of the invention are useful for acute treatment of cluster headache, that is, providing relief from one or more symptoms of cluster headache and/or shortening the duration of cluster headache.

The composition of the invention is preferably administered to the subject's pulmonary system, for example, using an inhaler, such as a dry powder inhaler, as described herein.

In one embodiment, the subject to be treated is an adult human. In another embodiment, the subject to be treated is a pediatric human, for example a human from about 6 to about 11 years of age, about 12 to about 17 years of age, or about 6 to about 17 years of age. In another embodiment, the subject is a human infant, for example, up to two years of age, a human of about 6 years of age or less.

As used herein, the term "therapeutically effective amount" means the amount needed to achieve the desired effect or efficacy. A therapeutically effective amount of a triptan composition for treating migraine or cluster headache is an amount of the triptan composition which provides relief from migraine or cluster headache or one or more symptoms of migraine or cluster headache. Such an amount of the triptan composition thereof preferably shortens the duration and/or intensity of a migraine or cluster headache or one or more symptoms thereof, such as pain and/or aura.

The actual effective amount of drug can vary according to the specific drug or combination thereof being utilized, the particular composition formulated, the mode of administration, and the age, weight, condition of the patient, and severity of the episode being treated.

In certain embodiments, the triptan formulation is administered to the subject two or more times for a single migraine episode or cluster headache. For example, a first dose can be administered to the subject, followed by a second or more doses at appropriate time intervals, such as about 1 or 2 hour intervals.

The present invention will be further understood by reference to the following non-limiting examples.

EXAMPLES

Example 1

Example 1: Evaluation of Different Excipients

Four excipients were compared as a part of this evaluation—L-leucine, Maltodextrin (DE=10.7%), Lactose, and Mannitol. Tables 3, 4, 5, and 6 provide a summary of the aerosol properties for L-leucine, Maltodextrins (DE=10.7%), Lactose, and Mannitol based formulations respectively. Table 7 summarizes the solid state properties of one L-leucine based and one Maltodextrin based formulation. Process parameters used for all these evaluations are summarized in Tables 29, 30, 31, and 32 respectively.

L-Leucine

Reagent grade L-leucine (Sigma Aldrich) was evaluated as a part of this study. Two Sumatriptan succinate loads (25% and 50%), three total solid concentrations of the spray drying solution (2 g/L, 4 g/L, and 6 g/L), and four solvent flow ratios (8:32 v:v Aqueous:Organic, 16:24 v:v Aqueous:Organic, 24:16 v:v Aqueous:Organic, and 32:8 v:v Aqueous:Organic) are evaluated with L-leucine. Process parameters used for this evaluation are detailed in Table 27. Table 1 below details the aerosol results obtained from this evaluation.

TABLE 1

Aerosol properties summary for L-leu based Sumatriptan succinate formulations

| Lot Number | 117077 | 117078 | 117079 | 117080 | 117081 | 117082 | 117083 | 117084 |
|---|---|---|---|---|---|---|---|---|
| Total solid concentration (g/L) | 2 | 4 | 6 | 4 | 2 | 4 | 6 | 4 |
| Sumatriptan succinate (%) | | 25 | | | | 50 | | |
| L-leucine (%) | | 55 | | | | 30 | | |
| Aqueous Flow (mL/min) | 8 | 16 | 24 | 32 | 8 | 16 | 24 | 32 |
| Organic flow (mL/min) | 32 | 24 | 16 | 8 | 32 | 24 | 16 | 8 |
| Fine particle fraction, <5.6 um (%) (Size 00) | 56 | 49 | 39 | 35 | 39 | 38 | 26 | 21 |
| Water content (%) | 1.69 | 2.18 | 2.03 | 1.75 | 1.87 | 2.68 | 1.52 | 1.39 |
| gPSD (VMGD 1 bar, mm) | 3.8 | 10.6 | 15.2 | 11.1 | 7.1 | 9.5 | 11.5 | 15.6 |
| Bulk/Aerated Density (g/cc) | 0.063 | 0.041 | 0.049 | 0.078 | 0.066 | 0.059 | 0.081 | 0.096 |
| Tap Density (g/cc) | 0.091 | 0.063 | 0.067 | 0.129 | 0.116 | 0.079 | 0.105 | 0.121 |

Formulations with the higher aqueous ratio are observed to produce particles with a lower FPF value and a higher gPSD, for both 25% and 50% Sumatriptan succinate formulations. Formulations with the higher aqueous ratios are also observed to produce more dense powder particles. In this and subsequent tables the amounts of Sumatriptan succinate and excipients are presented as fractions by weight of total solids.

Table 2 below details the solid state results obtained for the powder containing 50% Sumatriptan succinate and 30% L-leucine, spray dried at an Aqueous:Organic ratio of 24:16 v:v. and at a total solid concentration of 6 g/L.

TABLE 2

| Summary of Solid state properties for 50% Sumatriptan succinate formulation | |
|---|---|
| Lot Number | 117083 |
| Total solid concentration (g/L) | 6 |
| Sumatriptan succinate (%) | 50 |
| L-leucine | 30 |
| XRPD | PC-T1 |
| TGA-120 (%) | NT |
| Low T Endotherm 1/Tg (° C.) | 52.6 |
| Low T Endotherm 2/Tg (° C.) | 59.7 |
| Recrystallization Exotherm (° C.) | Broad |
| High T Melt Endotherm | Broad |

Maltodextrins

Maltodextrin having a dextrose equivalent of 10.7% (Sigma Aldrich) is evaluated as a part of this study. Three total solid concentrations of the spray drying solution (2 g/L, 4 g/L, and 6 g/L), and two solvent flow ratios (16:24 v:v Aqueous:Organic, and 24:16 v:v Aqueous:Organic) are evaluated with Maltodextrins (DE=10.7%). The Sumatriptan load is kept constant at 50%. Process parameters used for this evaluation are detailed in Table 28. Table 3 below details the results obtained from this evaluation.

TABLE 3

Aerosol properties summary for Maltodextrins based Sumatriptan succinate formulations

| Lot Number | 117091 | 117092 | 117093 | 117094 |
|---|---|---|---|---|
| Total solid concentration (g/L) | 2 | 4 | 2 | 4 |
| Sumatriptan succinate (%) | 50 | | | |
| Maltodextrins (DE = 10.7%) (%) | 30 | | | |
| Aqueous Flow (mL/min) | 16 | 16 | 24 | 24 |
| Organic flow (mL/min) | 24 | 24 | 16 | 16 |
| Fine particle fraction, <5.6 um (%) (Size 00) | 34 | 35 | 28 | 27 |
| Water content (%) | NT | NT | NT | NT |
| gPSD (VMGD 1 bar, mm) | 12.6 | 9.9 | 7.3 | 6.8 |
| Bulk/Aerated Density (g/cc) | 0.019 | 0.034 | 0.104 | 0.119 |
| Tap Density (g/cc) | 0.022 | 0.043 | 0.114 | 0.128 |

For both solvent ratios with Maltodextrin (DE=10.7%), the gPSD and FPF are observed to decrease and the density is observed to increase as the total solid concentration increases from 2 g/L to 4 g/L Table 4 below summarizes the solid state properties of the formulation spray dried at an Aqueous:Organic ratio of 16:26 v:v at 2 g/L total solid concentration.

TABLE 4

Solid state properties of Lot 117091

| Lot Number | 117091 |
|---|---|
| Total solid concentration (g/L) | 2 |
| Sumatriptan succinate (%) | 50 |
| Maltodextrins (%) | 30 |
| XRPD | A-T2 |
| TGA-120 (%) | NT |
| Low T Endotherm 1/Tg (° C.) | 42 |
| Low T Endotherm 2/Tg (° C.) | 49.3 |
| Recrystallization Exotherm (° C.) | None |
| High T Melt Endotherm | None |

Lactose

Inhalation grade lactose (DFE Pharma) was evaluated as a part of this study. Two total solid concentrations of the spray drying solution (2 g/L and 4 g/L), and two solvent flow ratios (16:24 v:v Aqueous:Organic and 24:16 Aqueous:Organic) were evaluated with Lactose. Process parameters used for this evaluation are detailed in Table 29. Table 5 below details the results obtained from this evaluation.

TABLE 5

Aerosol properties summary for Lactose based Sumatriptan succinate formulations

| Lot Number | 117103 | 117104 | 117105 | 117106 |
|---|---|---|---|---|
| Total solid concentration (g/L) | 2 | 4 | 2 | 4 |
| Sumatriptan succinate (%) | 50 | | | |
| Lactose (%) | 30 | | | |
| Aqueous Flow (mL/min) | 16 | 16 | 24 | 24 |
| Organic flow (mL/min) | 24 | 24 | 16 | 16 |
| Fine particle fraction, <5.6 um (%) (Size 00) | 23 | 28 | 22 | 21 |

TABLE 5-continued

Aerosol properties summary for Lactose based Sumatriptan succinate formulations

| Lot Number | 117103 | 117104 | 117105 | 117106 |
|---|---|---|---|---|
| Water content (%) | 2.36 | 2.31 | 3.89 | 4.22 |
| gPSD (VMGD 1 bar, mm) | 7.1 | 6.5 | 8.2 | 8.8 |
| Bulk/Aerated Density (g/cc) | 0.150 | 0.100 | 0.141 | 0.144 |
| Tap Density (g/cc) | 0.181 | 0.129 | 0.17 | 0.186 |

For both solvent ratios with Lactose, the gPSD, water content, and FPF are observed is observed to stay constant with varied total solid concentration and a constant Aqueous:Organic ratio.

Mannitol

USP grade Mannitol (BDH) was evaluated as a part of this study. Two total solid concentrations of the spray drying solution (2 g/L and 4 g/L), and two solvent flow ratios (16:24 v:v Aqueous:Organic and 24:16 Aqueous:Organic) were evaluated with Lactose. Process parameters used for this evaluation are detailed in Table 29. Table 6 below details the results obtained from this evaluation.

TABLE 6

Aerosol properties summary for Mannitol based Sumatriptan succinate formulations

| Lot Number | 117107 | 117108 | 117109 | 117110 |
|---|---|---|---|---|
| Total solid concentration (g/L) | 2 | 4 | 2 | 4 |
| Sumatriptan succinate (%) | 50 | | | |
| Mannitol (%) | 30 | | | |
| Aqueous Flow (mL/min) | 16 | 16 | 24 | 24 |
| Organic flow (mL/min) | 24 | 24 | 16 | 16 |
| Fine particle fraction, <5.6 um (%) (Size 00) | 31 | 27 | NT | NT |
| Water content (%) | 2.59 | 3.23 | NT | NT |
| gPSD (VMGD 1 bar, mm) | 5.4 | 6.9 | 44.7 | NT |
| Bulk/Aerated Density (g/cc) | 0.098 | 0.104 | 0.139 | NT |
| Tap Density (g/cc) | 0.147 | 0.126 | 0.156 | NT |

For the Mannitol based formulations, not enough powder was produced for the 24:16 Aqueous:Organic flow formulations. For the 16:24 Aqueous:Organic flow formulations, the FPF was observed to decrease and the gPSD, water content, and density were observed to increase as the total solid concentration increased from 2 g/L to 4 g/L.

Example 2: Increased Atomization Gas

This evaluation was performed to evaluate the effect of increased atomization gas on the gPSD and FPF of the resultant powder. For the purpose of this evaluation, a 50:30:18:2 Sumatriptan succinate:Maltodextrin:DPPC:NaCl formulation was spray dried using the process parameters described in Table 33. The Aqueous:Organic ratio was maintained at 20:80 v:v and the spray dryer outlet temperature was maintained at 44° C. Table 7 summarizes the aerosol data from this evaluation.

TABLE 7

Effect of increase in atomization gas flow on the properties of Maltodextrin based Sumatriptan succinate formulations

| Lot Number | 117153-1 | 117153-2 | 117153-3 |
|---|---|---|---|
| Total solid concentration (g/L) | 4 | 4 | 4 |
| Atomization gas flow rate | 22 | 33 | 44 |

TABLE 7-continued

Effect of increase in atomization gas flow on the properties of Maltodextrin based Sumatriptan succinate formulations

| Lot Number | 117153-1 | 117153-2 | 117153-3 |
|---|---|---|---|
| Fine particle fraction, <5.6 um (%) (Size 00) | 48 | 62 | 56 |
| Water content (%) | 3.8 | 3.91 | 3.72 |
| gPSD (VMGD 1 bar, mm) | 7.4 | 7.3 | 6.3 |
| Bulk/Aerated Density (g/cc) | 0.052 | 0.042 | 0.058 |
| Tap Density (g/cc) | 0.083 | 0.066 | 0.075 |

As expected, increasing the atomization gas flow rate is observed to slightly increase the FPF and decrease the gPSD of the powder formulation.

Example 3: Formulations Produced Using Maltodextrins Having Varied D.E. Values

Sumatriptan succinate Maltodextrins with four different Dextrose equivalent (D.E.) values were compared as a part of this study. Two atomizing gas air cap configurations (67147—single hole air cap, and 67-6-20-150—six hole air cap, both from Spraying systems company) and two liquid flow ratios (16:24 Aqueous:Organic v:v, and 24:16 Aqueous:Organic v:v) were evaluated. The spray drying outlet temperature was maintained at 44° C.

Three of these evaluations were performed using Maltodextrins procured from Sigma Chemicals Limited (St. Louis, Mo.), and the fourth evaluation was conducted using Maltodextrins acquired from Ingredion (Westchester, Ill.) and from Grain Processing Corporation (Muscatine, Iowa). The spray drying outlet temperature was maintained at 44° C. for all four evaluations.

1. Six Hole Air Cap at 20:80 Aqueous:Organic Ratio (Sigma Maltodextrins)

Four Maltodextrins from Sigma Chemicals were evaluated—Maltodextrin (DE=4.0-7.0%), Maltodextrin (DE=10.7%), Maltodextrin (DE=13.0-16.5%), and Maltodextrin (DE=16.0-19.0%) with a single hole air cap (Model 67147, Spraying systems Co.) at a 20:80 v:v Aqueous:Organic ratio.

Table 8 summarizes the formulation components and aerosol data for the first comparison listed above and Table 34 lists the process parameters used for this comparison.

TABLE 8

Aerosol properties of Sumatriptan succinate formulations with Maltodextrins from Sigma (20:80 Aq:Org ratio, 1-hole air cap)

| Lot Number | 117177 | 117178 | 117179 | 117180 |
|---|---|---|---|---|
| Total solid concentration (g/L) | 4 | 4 | 4 | 4 |
| Sumatriptan succinate (%) | 50 | 50 | 50 | 50 |
| Maltodextrin (DE = 4.0-7.0%) (%) | 30 | | | |
| Maltodextrin (DE = 10.7%) (%) | | 30 | | |
| Maltodextrin (DE = 13.0-16.5%) (%) | | | 30 | |
| Maltodextrin (DE = 16.0-19.0%) (%) | | | | 30 |
| DPPC (%) | 18 | 18 | 18 | 18 |
| Sodium chloride (%) | 2 | 2 | 2 | 2 |
| Fine particle fraction, <5.6 um (%) (Size 00) | 48 | 51 | 53 | 44 |
| Water content (%) | 5.74 | 4.5 | 4.82 | 5.49 |
| gPSD (VMGD 1 bar, mm) | 4.5 | 3.3 | 2.9 | 3.2 |
| Bulk/Aerated Density (g/cc) | 0.067 | 0.062 | 0.071 | 0.091 |
| Tap Density (g/cc) | 0.123 | 0.119 | 0.109 | 0.121 |

As seen in Table 8, all aerosol properties stay constant over the course of this evaluation. The only change seen is that the density of the powder is observed to increase as the dextrose equivalent value increases.

2. Six Hole Air Cap at 40:60 Aq:Org Ratio (Sigma Maltodextrins)

Four Maltodextrins from Sigma Chemicals were evaluated—Maltodextrin (DE=4.0-7.0%), Maltodextrin (DE=10.7%), Maltodextrin (DE=13.0-16.5%), and Maltodextrin (DE=16.0-19.0%) with a six hole air cap (Model 67-6-20-150, Spraying systems Co.)

Table 9 summarizes the formulation components and aerosol data for the second comparison listed above and Table 35 lists the process parameters used for this comparison.

TABLE 9

Aerosol properties of Sumatriptan succinate formulations with Maltodextrins from Sigma (20:80 Aq:Org ratio, 6-hole air cap)

| Lot Number | 117186 | 117188 | 117190 | 117191 |
|---|---|---|---|---|
| Total solid concentration (g/L) | 6 | 6 | 6 | 6 |
| Sumatriptan succinate (%) | 50 | 50 | 50 | 50 |
| Maltodextrin (DE = 4.0-7.0%) (%) | 30 | | | |
| Maltodextrin (DE = 10.7%) (%) | | 30 | | |
| Maltodextrin (DE = 13.0-16.5%) (%) | | | 30 | |
| Maltodextrin (DE = 16.0-19.0%) (%) | | | | 30 |
| DPPC (%) | 18 | 18 | 18 | 18 |
| Sodium chloride (%) | 2 | 2 | 2 | 2 |
| Fine particle fraction, <5.6 um (%) (Size 00) | 34 | 36 | 34 | 40 |
| Water content (%) | 4.76 | 5.02 | 5.11 | 4.44 |
| gPSD (VMGD 1 bar, mm) | 6.4 | 6.3 | 5.7 | 5.7 |
| Bulk/Aerated Density (g/cc) | 0.046 | 0.093 | 0.087 | 0.085 |
| Tap Density (g/cc) | 0.066 | 0.129 | 0.111 | 0.111 |

As seen in table 9 above, all four powders are observed to have lower FPF and densities, but slightly higher gPSDs as compared to the powders produced with a 20:80 ratio and the same nozzle during the first evaluation. However, these observations may also be due to a higher total solid concentration used in this evaluation.

3. Single Hole Air Cap at 40:60 Aq:Org Ratio (Sigma Maltodextrins)

Four Maltodextrins from Sigma Chemicals were evaluated—Maltodextrin (DE=4.0-7.0%), Maltodextrin (DE=10.7%), Maltodextrin (DE=13.0-16.5%), and Maltodextrin (DE=16.0-19.0%) with a single hole air cap (Model 67147, Spraying systems Co.) at a 20:80 v:v Aqueous:Organic ratio.

Table 10 summarizes the formulation components and aerosol data for the third comparison listed above and Table 36 lists the process parameters used for this comparison.

TABLE 10

Aerosol properties of Sumatriptan succinate formulations with Maltodextrins from Sigma (40:60 Aq:Org ratio, 1-hole air cap)

| Lot Number | 117164 | 117165 | 117166 | 117167 |
|---|---|---|---|---|
| Total solid concentration (g/L) | 6 | 6 | 6 | 6 |
| Sumatriptan succinate (%) | 50 | 50 | 50 | 50 |
| Maltodextrin (DE = 4.0-7.0%) (%) | 30 | | | |
| Maltodextrin (DE = 10.7%) (%) | | 30 | | |
| Maltodextrin (DE = 13.0-16.5%) (%) | | | 30 | |
| Maltodextrin (DE = 16.0-19.0%) (%) | | | | 30 |
| DPPC (%) | 18 | 18 | 18 | 18 |
| Sodium chloride (%) | 2 | 2 | 2 | 2 |
| Fine particle fraction, <5.6 um (%) (Size 00) | 49 | 44 | 45 | 50 |
| Water content (%) | NT | NT | NT | NT |
| gPSD (VMGD 1 bar, mm) | 3.9 | 4.2 | 4.1 | 4.4 |
| Bulk/Aerated Density (g/cc) | 0.097 | 0.135 | 0.124 | 0.135 |
| Tap Density (g/cc) | 0.152 | 0.147 | 0.143 | 0.157 |

As seen in Table 10 above, these powders seem to have a higher FPF and higher density but a lower gPSD as compared to the powders produced using a six hole nozzle at the same Aqueous:Organic ratio and total solid concentration.

4. Six Hole Air Cap at 20:80 Aq:Org Ratio (GPC and Ingredion Maltodextrins)

Two Maltodextrins from Ingredion (Stabilite SD-30, and Stabilite SD-60) and five Maltodextrins from Grain Processing Corporation (Maltrin M-100, Maltrin M-150, Maltrin M-180, Maltrin M-200, and Maltrin M-250) were evaluated. Table 11 summarizes the formulation components and aerosol data for the third comparison listed above and Table 37 lists the process parameters used for this fourth comparison.

TABLE 11

Aerosol properties of Sumatriptan succinate formulations with Maltodextrins from Ingredion & GPC (20:80 Aq:Org ratio, 6-hole air cap)

| Lot Number | 155039 | 155040 | 155034 | 155035 | 155036 | 155037 | 155038 |
|---|---|---|---|---|---|---|---|
| Total solid concentration (g/L) | 4 | 4 | 4 | 4 | 4 | 4 | 4 |
| Sumatriptan succinate (%) | 50 | 50 | 50 | 50 | 50 | 50 | 50 |
| Stabilite SD-30, Polyglycitol (%) | 30 | | | | | | |
| Stabilite SD-60, Polyglycitol (%) | | 30 | | | | | |
| Maltrin M-100, Maltodextrin (%) | | | 30 | | | | |
| Maltrin M-150, Maltodextrin (%) | | | | 30 | | | |
| Maltrin M-180, Maltodextrin (%) | | | | | 30 | | |
| Maltrin M-200, Corn syrup solids (%) | | | | | | 30 | |
| Maltrin M-250, Corn syrup solids (%) | | | | | | | 30 |
| DPPC (%) | 18 | 18 | 18 | 18 | 18 | 18 | 18 |
| Sodium chloride (%) | 2 | 2 | 2 | 2 | 2 | 2 | 2 |
| Fine particle fraction, <5.6 um (%) (Size 2) | 86 | 83 | 77 | 71 | 82 | 72 | 76 |
| Water content (%) | NT | NT | NT | NT | NT | NT | NT |
| gPSD (VMGD 1 bar, mm) | 2.3 | 3 | 2.7 | 2.5 | 2.3 | 2.3 | 2.4 |
| Bulk/Aerated Density (g/cc) | 0.07 | 0.06 | 0.06 | 0.08 | 0.08 | 0.06 | 0.08 |
| Tap Density (g/cc) | 0.11 | 0.11 | 0.1 | 0.12 | 0.12 | 0.13 | 0.13 |

FPF measurement for these powders was done using a size 2 capsule as opposed to size 00 capsules for the earlier evaluation. Values for FPF, gPSD, and densities for all powders were observed to be similar.

Example 4: Increased Spray Drying Outlet Temperature on L-Leu Based Formulation

Two spray drying outlet temperatures were evaluated—44° C. and 60° C. Additionally, Maltodextrins M-250 was compared to L-leucine at both spray dryer outlet temperatures. The Aqueous:Organic ratio used for all four powders was maintained at 20:80 v:v Process parameters for these evaluations are detailed in Table 38. Results for Fine particle fraction of these powders are listed in Table 12 below.

TABLE 12

FPF results for Sumatriptan succinate powders produced at varied spray dryer outlet temperatures

| Lot Number | 155046 | 155047 | 155048 | 155049 |
|---|---|---|---|---|
| Total solid concentration (g/L) | 4 | 4 | 4 | 4 |
| Outlet Temperature (° C.) | 44 | 60 | 44 | 60 |
| Sumatriptan succinate (%) | 50 | 50 | 50 | 50 |
| L-leucine (%) | | | 30 | 30 |
| Maltrin M-250, Corn syrup solids (%) | 30 | 30 | | |
| DPPC (%) | 18 | 18 | 18 | 18 |
| Sodium chloride (%) | 2 | 2 | 2 | 2 |
| Fine particle fraction, <5.6 um (%) (Size 00) | 61 | 51 | 40 | 36 |
| Fine particle fraction, <5.6 um (%) (Size 2) | 80 | 66 | 53 | 46 |

Powders produced at 44° C. were observed to have a higher FPF value as compared to powders produced at 60° C. Additionally, powders produced with Maltrin M-250 were observed to have a higher FPF as compared to the L-leucine powders.

Example 5: Varied Sumatriptan Succinate Loads at 44° C. Spray Dryer Outlet Temperature The effect of Sumatriptan succinate load on the aerosol and solid state properties of spray dried Sumatriptan succinate powder produced at an outlet temperature of 44° C. was evaluated for this study. Sumatriptan succinate load was varied from 40% to 70%, for which the L-leucine load was decreased from 40% to 10%. The DPPC ratio was maintained at 18%, and the Sodium chloride ratio was maintained at 2%. Aerosol data from these powders is summarized in Table 13 below. Process parameters used for this evaluation are detailed in Table 39.

TABLE 13

FPF results with increased Sumatriptan succinate load at 44 C. spray dryer outlet temp

| Lot Number | 155004 | 155005 | 155006 | 155007 |
|---|---|---|---|---|
| Total solid concentration (g/L) | 4 | 4 | 4 | 4 |
| Sumatriptan succinate (%) | 40 | 50 | 60 | 70 |
| L-leucine (%) | 40 | 30 | 20 | 10 |
| DPPC (%) | | | 18 | |
| Sodium chloride (%) | | | 2 | |
| Fine particle fraction, <5.6 um (%) (Size 00) | 52 | 35 | 46 | 37 |
| Fine particle fraction, <5.6 um (%) (Size 2) | 54 | 49 | 45 | 32 |
| Water content (%) | NT | NT | 3.33 | 2.98 |
| gPSD (VMGD 1 bar, mm) | 2.5 | 2.6 | 2.4 | 2.8 |
| Bulk/Aerated Density (g/cc) | 0.089 | 0.091 | 0.129 | 0.142 |
| Tap Density (g/cc) | 0.128 | 0.142 | 0.176 | 0.226 |

The FPF of the formulations is observed to decrease as the Sumatriptan succinate load increases. Both the particle size and the density values are observed to go up as the drug load goes up. In this and subsequent tables the FPF values presented are measured using only size 2 capsules.

Example 6: Varied DPPC Loads at 44° C. Spray Dryer Outlet Temperature

The effect of DPPC load on the aerosol and solid state properties of spray dried Sumatriptan succinate powder produced at an outlet temperature of 44° C. was evaluated for this study. Four DPPC loads are evaluated—8%, 18%, 28%, and 38% and the Sumatriptan succinate load is kept constant. An increase in the DPPC load is balanced by decreasing the L-leucine load of the formulation. Table 40 details the process parameters used for this evaluation. Table 14 details the aerosol results for the four powders produced during this evaluation.

TABLE 14

FPF results with increased DPPC load at 44 C. spray dryer outlet temp

| Lot Number | 155018 | 155019 | 155020 | 155021 |
|---|---|---|---|---|
| Total solid concentration (g/L) | 4 | 4 | 4 | 4 |
| Sumatriptan succinate (%) | | | 50 | |
| L-leucine (%) | 40 | 30 | 20 | 10 |
| DPPC (%) | 8 | 18 | 28 | 38 |
| Sodium chloride (%) | | | 2 | |
| Fine particle fraction, <5.6 um (%) (Size 2) | 51 | 55 | 53 | 48 |
| gPSD (VMGD 1 bar, mm) | 6.5 | 5.3 | 5 | 5.5 |
| Bulk/Aerated Density (g/cc) | 0.064 | 0.069 | 0.077 | 0.103 |
| Tap Density (g/cc) | 0.093 | 0.096 | 0.108 | 0.133 |

The FPF and gPSD are observed to stay constant as the DPPC load increases. However, the density values are observed to increase as the DPPC load increases.

Example 7: Comparison of Different Maltodextrins (Spray Dryer Outlet Temperatures of 50 and 60° C.)

Two Maltodextrins from Ingredion (Stabilite SD-30, and Stabilite SD-60) and five Maltodextrins from Grain Processing Corporation (Maltrin M-100, Maltrin M-150, Maltrin M-180, Maltrin M-200, and Maltrin M-250) were evaluated during this study.

1. Spray Dryer Outlet Temperature of 50° C.

Four Maltodextrins were evaluated at 50° C.-SD-30, SD-60, M-200, and M-250. The Aqueous:Organic ratio was maintained at 20:80 v:v at a total liquid flow rate of 40 mL/min. Process parameters listed in Table 41 are used to produce this powder. Results from this evaluation are shown in Table 15 below.

TABLE 15

Aerosol results from Sumatriptan succinate powders spray dried at 50 C.

| Lot Number | 155043 | 155044 | 155041 | 155042 |
|---|---|---|---|---|
| Total solid concentration (g/L) | 4 | 4 | 4 | 4 |
| Sumatriptan succinate (%) | 50 | 50 | 50 | 50 |
| Stabilite SD-30, Polyglycitol (%) | 30 | | | |
| Stabilite SD-60, Polyglycitol (%) | | 30 | | |
| Maltrin M-200, Corn syrup solids (%) | | | 30 | |
| Maltrin M-250, Corn syrup solids (%) | | | | 30 |
| DPPC (%) | 18 | 18 | 18 | 18 |
| Sodium chloride (%) | 2 | 2 | 2 | 2 |
| Fine particle fraction, <5.6 um (%) (Size 2) | 76 | 78 | 80 | 76 |
| Water content (%) | | | | |
| gPSD (VMGD 1 bar, mm) | 2.1 | 2.3 | 2.3 | 2.6 |
| Bulk/Aerated Density (g/cc) | 0.08 | 0.08 | 0.08 | 0.08 |
| Tap Density (g/cc) | 0.15 | 0.13 | 0.14 | 0.13 |

Values for FPF, gPSD, bulk density, and tap density for all four maltodextrin powders are observed to stay consistent for all four Maltodextrins.

2. Spray Dryer Outlet Temperature of 60° C.

Seven Maltodextrins are evaluated at 60° C.-SD-30, SD-60, M-100, M-150, M-180, M-200, and M-250. The Aqueous:Organic ratio was maintained at 20:80 v:v at a total liquid flow rate of 40 mL/min. Process parameters listed in Table 42 are used to produce this powder. Results from this evaluation are shown in Table 16 below.

TABLE 16

Aerosol results from Sumatriptan succinate powders spray dried at 60 C.

| Lot Number | 155059 | 155060 | 155061 | 155062 | 155063 | 155064 | 155065 |
|---|---|---|---|---|---|---|---|
| Total solid concentration (g/L) | 4 | 4 | 4 | 4 | 4 | 4 | 4 |
| Sumatriptan succinate (%) | 50 | 50 | 50 | 50 | 50 | 50 | 50 |
| Stabilite SD-30, Polyglycitol (%) | | | | | | | 30 |
| Stabilite SD-60, Polyglycitol (%) | | | | | | 30 | |
| Maltrin M-100, Maltodextrin (%) | | | | | 30 | | |
| Maltrin M-150, Maltodextrin (%) | | | | 30 | | | |
| Maltrin M-180, Maltodextrin (%) | | | 30 | | | | |
| Maltrin M-200, Corn syrup solids (%) | | 30 | | | | | |

TABLE 16-continued

Aerosol results from Sumatriptan succinate powders spray dried at 60 C.

| Lot Number | 155059 | 155060 | 155061 | 155062 | 155063 | 155064 | 155065 |
|---|---|---|---|---|---|---|---|
| Maltrin M-250, Corn syrup solids (%) | 30 | | | | | | |
| DPPC (%) | 18 | 18 | 18 | 18 | 18 | 18 | 18 |
| Sodium chloride (%) | 2 | 2 | 2 | 2 | 2 | 2 | 2 |
| Fine particle fraction, <5.6 um (%) (Size 00) | 34 | 48 | 45 | 48 | 46 | 46 | 44 |
| Fine particle fraction, <5.6 um (%) (Size 2) | 51 | 54 | 57 | 62 | 62 | 52 | 52 |
| Water content (%) | 3.43 | 2.32 | 2.23 | 2 | 2.71 | 2.86 | 3.36 |
| gPSD (VMGD 1 bar, mm) | 11.2 | 9.4 | 7.3 | 6.1 | 7 | 7.2 | 7.9 |
| Bulk/Aerated Density (g/cc) | 0.020 | 0.033 | 0.049 | 0.067 | 0.072 | 0.069 | 0.065 |
| Tap Density (g/cc) | 0.033 | 0.057 | 0.076 | 0.085 | 0.097 | 0.102 | 0.088 |

Values for FPF and water content are observed to stay consistent for all four Maltodextrins. However, particles produced with the M-200 and M-250 are observed to have a relatively lower density value and a relatively higher gPSD value as compared to the other maltodextrins.

Example 8: Spray Dryer Setup Configurations

This study is conducted to evaluate different spray drying configurations for the production of SD-30 based Sumatriptan succinate formulations. Table 17 below details the spray dryer configurations and the results from evaluating these powders. Parameters used for the production of these powders are listed in Table 43.

Additional studies described in the following examples are conducted to evaluate the cause of moist deposits as well as the reason for non-comparable data for powders produced on the Automatic Spray dryer and the Manual Spray dryer.

Example 9: Varied Sumatriptan Succinate Loads at 60° C. Outlet Temperature

The effect of Sumatriptan succinate load on the aerosol and solid state properties of spray dried Sumatriptan succinate powder produced at an outlet temperature of 60° C. was evaluated for this study. Sumatriptan succinate load was varied from 50% to 50%, for which the L-leucine or SD-30

TABLE 17

| Sumatriptan succinate powder spray dried with varied spray dryer configurations | | | | | | | | |
|---|---|---|---|---|---|---|---|---|
| Lot Number | 155091 | 155092 | 155094 | 155095 | 155097 | 155098 | 155100-1 | 155100-2 |
| Total solid concentration (g/L) | 4 | 4 | 4 | 4 | 4 | 4 | 4 | 4 |
| Sumatriptan succinate (%) | 50 | 50 | 50 | 50 | 50 | 50 | 50 | 50 |
| Stabilite SD-30, Polyglycitol (%) | 30 | 30 | 30 | 30 | 30 | 30 | 30 | 30 |
| DPPC (%) | 18 | 18 | 18 | 18 | 18 | 18 | 18 | 18 |
| Sodium chloride (%) | 2 | 2 | 2 | 2 | 2 | 2 | 2 | 2 |
| Fine particle fraction, <5.6 um (%) (Size 00) | 69 | 42 | 68 | 43 | | | | |
| Fine particle fraction, <5.6 um (%) (Size 2) | 80 | 60 | 82 | 56 | 67 | 66 | 84 | 78 |
| Bulk/Aerated Density (g/cc) | | | 0.079 | 0.065 | 0.073 | 0.086 | 0.089 | 0.076 |
| Tap Density (g/cc) | | | 0.113 | 0.098 | 0.114 | 0.132 | 0.132 | 0.118 |
| Configuration | Bottom inlet product filter with Manual spray dryer unit (control) | Top inlet product filter with Automatic spray dryer unit | Bottom inlet product filter with Manual spray dryer unit (control) | Top inlet product filter with Automatic spray dryer unit | Bottom inlet product filter with Automatic spray dryer unit (Nozzle # 1) - Moist deposits on piping observed | Bottom inlet product filter with Automatic spray dryer unit (Nozzle # 2)- Moist deposits on piping observed | Bottom inlet product filter with Manual spray dryer unit (control) | Top inlet product filter with Manual spray dryer unit | load was decreased from 75% to 30%. The DPPC ratio was maintained at 18%, and the Sodium chloride ratio was maintained at 2%.

1. L-Leucine Based Formulations

Process parameters used for this evaluation are described in Table 44. Table 18 details the results from this evaluation.

TABLE 18

Varied Sumatriptan succinate load for L-leu based formulation (60 C.)

| Lot Number | 155104 | 155105 | 155106 | 155107 | 155108 | 155109 | 155110 | 155111 | 155112 | 155113 |
|---|---|---|---|---|---|---|---|---|---|---|
| Total solid concentration (g/L) | 4 | 4 | 4 | 4 | 4 | 4 | 4 | 4 | 4 | 4 |
| Sumatriptan succinate (%) | 5 | 10 | 15 | 20 | 25 | 30 | 35 | 40 | 45 | 50 |
| L-leucine (%) | 75 | 70 | 65 | 60 | 55 | 50 | 45 | 40 | 35 | 30 |
| DPPC (%) | 18 | 18 | 18 | 18 | 18 | 18 | 18 | 18 | 18 | 18 |
| Sodium chloride (%) | 2 | 2 | 2 | 2 | 2 | 2 | 2 | 2 | 2 | 2 |
| Fine particle fraction, <5.6 um (%) (Size 2) | 77 | 74 | 71 | 70 | 71 | 58 | 61 | 61 | 64 | 66 |
| Water content (%) | | | | | | | | | | |
| gPSD (VMGD 1 bar, mm) | 2.2 | 2.3 | 2.5 | 2.1 | 2 | 2.3 | 2.4 | 2.7 | 3.4 | 3.1 |
| Bulk/Aerated Density (g/cc) | 0.087 | 0.093 | 0.087 | 0.092 | 0.104 | 0.104 | 0.107 | 0.103 | 0.103 | 0.092 |
| Tap Density (g/cc) | 0.120 | 0.134 | 0.124 | 0.116 | 0.135 | 0.161 | 0.144 | 0.128 | 0.129 | 0.165 |

As the Sumatriptan succinate increases, the FPF value is observed to decrease slightly and the gPSD is observed to increase slightly. Both bulk and tap density values stay relatively constant.

2. SD-30 Based Formulations

Process parameters used for this evaluation are mentioned in Table 45. Table 19 details the results from this evaluation.

TABLE 19

Varied Sumatriptan succinate load for SD-30 based formulation (60 C.)

| Lot Number | 155125 | 155126 | 155127 | 155128 | 155129 | 155130 | 155131 | 155132 | 155133 | 155134 |
|---|---|---|---|---|---|---|---|---|---|---|
| Total solid concentration (g/L) | 4 | 4 | 4 | 4 | 4 | 4 | 4 | 4 | 4 | 4 |
| Sumatriptan succinate (%) | 5 | 10 | 15 | 20 | 25 | 30 | 35 | 40 | 45 | 50 |
| Stabilite SD-30, Polyglycitol (%) | 75 | 70 | 65 | 60 | 55 | 50 | 45 | 40 | 35 | 30 |
| DPPC (%) | 18 | 18 | 18 | 18 | 18 | 18 | 18 | 18 | 18 | 18 |
| Sodium chloride (%) | 2 | 2 | 2 | 2 | 2 | 2 | 2 | 2 | 2 | 2 |
| Fine particle fraction, <5.6 um (%) (Size 2) | 60 | 55 | 71 | 70 | 76 | 65 | 70 | 70 | 67 | 71 |
| Bulk/Aerated Density (g/cc) | 0.093 | 0.143 | 0.085 | 0.098 | 0.092 | 0.086 | 0.081 | 0.065 | 0.101 | 0.096 |
| Tap Density (g/cc) | 0.120 | 0.168 | 0.115 | 0.130 | 0.156 | 0.113 | 0.111 | 0.087 | 0.133 | 0.166 |
| XRPD | | A-T2 | | A-T2 | A-T2 | A-T2 | | A-T2 | | A-T2 |
| TGA-120 (%) | | 4.48 | | 3.17 | 2.67 | 1.71 | | 1.45 | | 2.14 |
| Low T Endotherm 1/Tg (° C.) | | 41.6 (sharp) | | 42.2 (sharp) | 42 | 42.3 | | 42.5 | | 43.6 |
| Low T Endotherm 2/Tg (° C.) | | none | | none | none | 61.1 (small) | | 63.2 (small) | | 62.9 (small) |
| Recrystallization Exotherm (° C.) | | none | | none | none | none | | none | | none |
| High T Melt Endotherm | | none | | none | none | none | | none | | none |

Legend for Solid state data: A-T2: Diffractogram is amorphous with the exception of 1-2 peaks associated with the excipients, Tg: Glass transition intercept As the Sumatriptan succinate increases, the FPF observed to decrease slightly and the gPSD is observed to increase slightly. Both bulk and tap density values stay relatively constant.

Example 10: Stability of SD-30 Formulations Produced at Varied Spray Dryer Outlet Temperatures Three spray dryer outlet temperatures are evaluated with the SD-30 based formulation—44° C., 50° C., and 60° C. Process parameters used for this evaluation are listed in Table 46. Table 20 summarizes the aerosol properties of these formulations at t=0, and t=2 week and 1 month at 40° C. storage conditions. Table 21 summarizes the solid state data over the course of this stability study.

TABLE 20

Aerosol data for SD-30 based powders produced at varied outlet temperatures

| Lot # | Formulation | Condition | | VMGD (um) | FPF (%) |
|---|---|---|---|---|---|
| 189065-1 | 30:50:18:2 SumatriptanS:SD-30:DPPC:NaCl (Outlet = 60) | 40 C. | t = 0<br>1 week<br>1 month | 7.5 | 60<br>61<br>68 |
| 189065-2 | 30:50:18:2 SumatriptanS:SD-30:DPPC:NaCl (Outlet = 50) | 40 C. | t = 0<br>1 week<br>1 month | 5 | 69<br>67<br>67 |
| 189065-3 | 30:50:18:2 SumatriptanS:SD-30:DPPC:NaCl (Outlet = 44) | 40 C. | t = 0<br>1 week<br>1 month | 6.2 | 75<br>73<br>67 |

The FPF value for all three formulations stays consistent throughout the stability evaluation. No evidence of API crystallization/nucleation was observed by XRPD or DSC. Endothermic shifting observed from t=0 with growth of peak in the 50-53 C area, likely due to DPPC phase transition/transformation. All samples have consistent weight loss by TGA. No clear physical differences between formulations from solid state characterization. 189065-1 (highest outlet) may have higher % of initial "transformed" DPPC as evident by 2nd endotherm (~50's C) and what appears to be less thermal crystallization.

TABLE 21

Solid state data for SD-30 based powders produced at varied outlet temperatures

| Lot # | Formulation | Condition | | XRPD | TGA-120 (%) | Low T 1 (° C.) | Low T 2 (° C.) | Recryst. (° C.) | Recryst. ΔH (J/g) | Melt (° C.) |
|---|---|---|---|---|---|---|---|---|---|---|
| 189065-1 | 30:50:18:2 SumatriptanS:SD-30:DPPC:NaCl (Outlet = 60) | 40 C. | t = 0<br>1 week<br>1 month | A-T2<br>A-T2<br>A-T2 | 2.39<br>1.78<br>1.71 | 38.1 (Tg)<br>39.6 (Tg)<br>39.7 (Tg) | 41.8, 58.7<br>42.4, 52.8<br>42.7, 54.2 | unclear<br>none<br>none | n.c.<br>none<br>none | none<br>none<br>none |
| 189065-2 | 30:50:18:2 SumatriptanS:SD-30:DPPC:NaCl (Outlet = 50) | 40 C. | t = 0<br>1 week<br>1 month | A-T2<br>A-T2<br>A-T2 | 2.22<br>1.69<br>1.80 | 38.7 (Tg)<br>39.7 (Tg)<br>40.0 (Tg) | 41.6<br>42.6, 53.0<br>42.9, 54.0 | 67.7<br>69.8 (broad)<br>69.9 (broad) | n.c.<br>n.c.<br>n.c. | none<br>none<br>none |
| 189065-3 | 30:50:18:2 SumatriptanS:SD-30:DPPC:NaCl (Outlet = 44) | 40 C. | t = 0<br>1 week<br>1 month | A-T2<br>A-T2<br>A-T2 | 1.96<br>1.57<br>1.39 | 38.6 (Tg)<br>40.3 (Tg)<br>40.6 (Tg) | 41.6<br>42.7, 53.1*<br>43.2, 53.9 | 67.9 (broad)<br>74.2 (broad)<br>73.5 (broad) | n.c.<br>n.c.<br>n.c. | Unk 153, 164<br>none<br>none |

1. "n.c." = not calculated due to size, shape, or proximity to other events. Event is small
2. Unk = unknown events possibly related to artifacts or small melts from thermal crystallization (not observed in 40 C. samples).
3. *estimated value
4. A-T2: Diffractogram is amorphous with the exception of 1-2 peaks associated with the excipients
5. Tg: Glass transition intercept.

Example 11: Comparison of Formulations Produced with a 6-Hole Air Cap and a 1-Hole Air Cap This evaluation was conducted to compare the stability two variations over 3 months at 40° C.—(i) varied air cap configurations with varied Aqueous:Organic ratios at a higher outlet temperature, and (ii) varied outlet temperatures with same air-cap configurations. Both the SD-30 based formulations and the L-leucine formulations were evaluated.
1. SD-30 Based Formulations Table 22 summarizes the aerosol stability data and Table 23 summarizes the solid state stability data. Process parameters used for the production of the 6-hole air cap formulation are listed in Table 47. Process parameters used for the production of the 1-hole air cap formulations are listed in Table 48.

TABLE 22

Aerosol data for SD-30 based formulations evaluated for Air cap config, Aq:Org ratio and Outlet temp.

| Lot # | Formulation | Condition | | VMGD (um) | pBulk (g/cc) | pTap (g/cc) | FPF (%) |
|---|---|---|---|---|---|---|---|
| 189111 | 30:50:18:2 SumatriptanS:SD-30:DPPC:NaCl | 20 C. | t = 0<br>2 week<br>1 month | 6.3<br>7.6<br>7.3 | 0.04 | 0.05 | 59<br>66<br>71 |

TABLE 22-continued

Aerosol data for SD-30 based formulations evaluated for Air cap config, Aq:Org ratio and Outlet temp.

| Lot # | Formulation | Condition | | VMGD (um) | pBulk (g/cc) | pTap (g/cc) | FPF (%) |
|---|---|---|---|---|---|---|---|
| | (6-hole air cap, 60 C. outlet) | | 3 month | | | | 65 |
| | | | 6 month | | | | |
| | | 40 C. | 2 week | 6.9 | | | 63 |
| | | | 1 month | 6.4 | | | 58 |
| | | | 3 month | | | | 56 |
| |

TABLE 23-continued

Solid state data for SD-30 based formulations evaluated for Air cap config, Aq:Org ratio and Outlet temp.

| Lot # | Formulation | Condition | XRPD | TGA-120 (%) | Low T 1 (° C.) | Low T 2 (° C.) | Recryst. (° C.) | Recryst. ΔH (J/g) | Melt (° C.) |
|---|---|---|---|---|---|---|---|---|---|
| | | 3 month | A-T2 | 1.63 | 48.1 (Tg1), 53.6 (Tg2) | 54.9 | 66.9, 93.5, 141.4 | n.c., n.c., n.c. | none |
| | | 6 month | A-T2 | 1.7 | 43.3 (Tg)**** | 55.3 | 67.8, 105.4 | n.c., n.c. | none |

1. "n.c." = not calculated due to size, shape, or proximity to other events. Event is small.
2. Unk = unknown events possibly related to artifacts or small melts from thermal crystallization (not observed in 40 C. samples).
3. A-T2: Diffractogram is amorphous with the exception of 1-2 peaks associated with the excipients
4. Tg: Glass transition intercept
5. **Tg for 189111 1M40C is calcualted as part of a shoulder within the endotherm. This method may not accurately reflect the correct Tg value of this event is a true Tg.
6. ***Tg for 189108 1M40C shows shoulder within endotherm indicating the Tg value may be lower than what is reported.

2. L-Leucine Based Formulations

Two Sumatriptan succinate loads are evaluated with L-leucine—20% and 30%. Table 25 summarizes the aerosol data and Table 26 summarizes the solid state data at t=0 and over the course of one month storage at both 20 C and 40 C (With time points at 2 weeks and 1 month). Process parameters used for the production of these 1-hole air cap formulations are listed in Table 48.

TABLE 25

| Lot # | Formulation | Condition | | | VMGD (um) | pBulk (g/cc) | pTap (g/cc) | FPF (%) |
|---|---|---|---|---|---|---|---|---|
| 189121 | 20:60:18:2 Sumatriptan succinate:L-leucine:DPPC:NaCl | | t = 0 | | 12.4 | 0.07 | 0.09 | 49 |
| | | 20 C. | Capsules | 1 week | 13.2 | | | 53 |
| | | | | 2 weeks | 12.7 | | | 49 |
| | | | | 1 month | 12.3 | | | 46 |
| | | | Bulk powder in vials | 1 week | | | | 59 |
| | | | | 2 weeks | | | | 53 |
| | | | | 1 month | | | | 45 |
| | | 40 C. | Capsules | 1 week | 12.9 | | | 42 |
| | | | | 2 weeks | 14.5 | | | 41 |
| | | | | 1 month | 13.7 | | | 34 |
| | | | Bulk powder in vials | 1 week | | | | 45 |
| | | | | 2 weeks | | | | 68 |
| | | | | 1 month | | | | 39 |
| 189122 | 30:50:18:2 Sumatriptan succinate:L-leucine:DPPC:NaCl | | t = 0 | | 11.2 | 0.07 | 0.12 | 48 |
| | | 20 C. | Capsules | 1 week | 11.8 | | | 51 |
| | | | | 2 weeks | 11.4 | | | 50 |
| | | | | 1 month | 11.4 | | | 44 |
| | | | Bulk powder in vials | 1 week | | | | 49 |
| | | | | 2 weeks | | | | 49 |
| | | | | 1 month | | | | 48 |
| | | 40 C. | Capsules | 1 week | 15.3 | | | 39 |
| | | | | 2 weeks | 15.3 | | | 39 |
| | | | | 1 month | 15.6 | | | 33 |
| | | | Bulk powder in vials | 1 week | | | | 45 |
| | | | | 2 weeks | | | | 44 |
| | | | | 1 month | | | | 38 |

The FPF values are consistently lower than the SD-30 based formulation. The gPSD values are significantly higher than the SD-30 based formulation. No evidence of API crystallization/nucleation observed except for 40 C 1 Month Capsule for 189121 shows hint of nucleation by XRD. Unclear glass transition behavior, potential sub Tg events. The value that was initially calculated as "sub Tg" may in fact be the Tg or potentially one of the Tg events in a multi Tg systems (which would indicate a lack of homogeneity). Potential thermal crystallization of API observed by DSC in the 80-150 C region. Weight loss by TGA remains stable though 1M samples show systemic drop in weight loss.

TABLE 26

| Lot # | Formulation | Condition | | | XRPD | TGA-120 (%) | Low T 1 (° C.) | Low T 2 (° C.) | Recryst. (° C.) | Recryst. ΔH (J/g) | Melt (° C.) |
|---|---|---|---|---|---|---|---|---|---|---|---|
| 189121 | 20:60:18:2 Sumatriptan | | t = 0 | | PC-T2 | 0.96 | no clear Tg | 51.6, 63.2 | none | none | none |
| | | 20 C. | Capsules | 1 week | PC-T2 | 1.08 | no clear Tg | 51.1, 63.1 | none | none | none |

TABLE 26-continued

| Lot # | Formulation | Condition | | XRPD | TGA-120 (%) | Low T 1 (° C.) | Low T 2 (° C.) | Recryst. (° C.) | Recryst. ΔH (J/g) | Melt (° C.) |
|---|---|---|---|---|---|---|---|---|---|---|
| | succinate:L-leucine:DPPC:NaCl | | 2 weeks | PC-T2 | 0.94 | no clear Tg | 50.9, 63.1 | 83.2 (broad) | n.c. | none |
| | | | 1 month | PC-T2 | 0.21 | 34.3 (Tg? unclear) | 52.3, 62.8 | none | none | none |
| | | Bulk powder in vials | 1 week | NT | NT | NT | NT | NT | NT | NT |
| | | | 2 weeks | PC-T2 | 1.19 | no clear Tg | 51.4, 63.4 | 81.5 (broad) | n.c. | none |
| | | | 1 month | PC-T2 | 0.50 | 36.3 (Tg? unclear) | 54.0, 64.0 | small (broad) | n.c. | none |
| | | 40 C. Capsules | 1 week | PC-T2 | 1.21 | no clear Tg | 50.1, 63.7 | 149.6 | 11.2 | none |
| | | | 2 weeks | PC-T2 | 1.11 | no clear Tg | 51.6, 63.9 | 98.3, 146.1 (unclear) | n.c. | none |
| | | | 1 month | PC | 0.56 | 27.4 (sub Tg?) | 52.2, 64.1 | 99.2 (broad) | n.c. | none |
| | | Bulk powder in vials | 1 week | NT | NT | NT | NT | NT | NT | NT |
| | | | 2 weeks | PC-T2 | 1.15 | no clear Tg | 51.6, 63.8 | 88.2, 144.2 (unclear) | n.c. | none |
| | | | 1 month | PC-T2 | 0.35 | 35.9 (sub Tg?) | 52.8, 63.6 | small (broad) | n.c. | none |
| 189122 | 30:50:18:2 Sumatriptan succinate:L-leucine:DPPC:NaCl | | t = 0 | PC-T2 | 1.28 | no clear Tg | 51.1, 63.2 | none | none | none |
| | | 20 C. Capsules | 1 week | PC-T2 | 1.02 | no clear Tg | 50.4, 62.8 | none | none | none |
| | | | 2 weeks | PC-T2 | 1.18 | no clear Tg | 50.1, 62.6 | unclear (broad) | n.c. | none |
| | | | 1 month | PC-T2 | 0.51 | 29.3 (sub Tg?) | 50.9, 62.2 | unclear (broad) | n.c. | none |
| | | Bulk powder in vials | 1 week | NT | NT | NT | NT | NT | NT | NT |
| | | | 2 weeks | PC-T2 | 1.51 | no clear Tg | 50.7, 62.9 | unclear (broad) | n.c. | none |
| | | | 1 month | PC-T2 | 0.40 | 26.8 (sub Tg?) | 51.2, 62.6 | unclear (broad) | n.c. | none |
| | | 40 C. Capsules | 1 week | PC-T2 | 1.41 | no clear Tg | 50.0, 63.7 | 150.6 | 1.87 | none |
| | | | 2 weeks | PC-T2 | 1.47 | no clear Tg | 49.4, 63.2 | 92.3 (small, broad?) | n.c. | none |
| | | | 1 month | PC-T2 | 0.82 | 30.8 (sub Tg?) no clear Tg | 52.2, 63.1 | 100 (broad), 154, 170 | n.c. | |
| | | Bulk powder in vials | 1 week | NT | NT | NT | NT | NT | NT | NT |
| | | | 2 weeks | PC-T2 | 1.60 | no clear Tg | 50.7, 63.4 | none | none | none |
| | | | 1 month | PC-T2 | 0.41 | 34.2 (sub Tg?) no clear Tg | 51.6, 62.5 | 100 broad, 167 | n.c | none |

1. "n.c." = not calculated due to size, shape, or proximity to other events. Event is small.
2. A-T2: Diffractogram is amorphous with the exception of 1-2 peaks associated with the excipients
3. Tg: Glass transition intercept
4. ***Drop in Tg may be due to appearance of separation between Tg and initial endotherm, which in previous samples overlapped resulting in a higher Tg intercept calculation.
5. The value that was initially calculated as "sub Tg" may in fact be the Tg or potentially one of the Tg events in a multi Tg systems (which would indicate a lack of homogeneity)

3. Spray Drying Process Parameters

TABLE 27

| Lot Number | 117048 | 117049 | 117050 |
|---|---|---|---|
| Total solid concentration (g/L) | 4 | 4 | 4 |
| Inlet Temperature (° C.) | 78 | 78 | 78 |
| Outlet Temperature (° C.) | 44 | 44 | 44 |
| Drying Gas Rate (kg/hr) | 100 | 100 | 100 |
| Atomization Gas Flow Rate (g/min) | 22 | 22 | 22 |
| Aqueous Flow (mL/min) | 8 | 8 | 8 |
| Organic flow (mL/min) | 32 | 32 | 32 |
| Product filter purge gas flow (scfh) | 15 | 15 | 15 |
| Sumatriptan succinate (%) | 5 | 20 | 50 |
| L-leucine (%) | 75 | 60 | 30 |
| DPPC (%) | 18 | 18 | 18 |
| Sodium chloride (%) | 2 | 2 | 2 |

TABLE 28

| Lot Number | 117072 | 117073 |
|---|---|---|
| Total solid concentration (g/L) | 4 | 4 |
| Inlet Temperature (° C.) | 78 | 106 |
| Outlet Temperature (° C.) | 44 | 60 |
| Drying Gas Rate (kg/hr) | 100 | 100 |
| Atomization Gas Flow Rate (g/min) | 22 | 22 |
| Aqueous Flow (mL/min) | 8 | 8 |
| Organic flow (mL/min) | 32 | 32 |
| Product filter purge gas flow (scfh) | 15 | 15 |
| Sumatriptan succinate (%) | 80 | 80 |
| L-leucine (%) | | |
| DPPC (%) | 18 | 18 |
| Sodium chloride (%) | 2 | 2 |

TABLE 29

| Lot Number | 117077 | 117078 | 117079 | 117080 | 117081 | 117082 | 117083 | 117084 |
|---|---|---|---|---|---|---|---|---|
| Total solid concentration (g/L) | 2 | 4 | 6 | 4 | 2 | 4 | 6 | 4 |
| Inlet Temperature (° C.) | 78 | 91 | 100 | 108 | 78 | 85 | 95 | 104 |
| Outlet Temperature (° C.) | 44 | 44 | 44 | 44 | 44 | 44 | 44 | 44 |
| Drying Gas Rate (kg/hr) | 100 | 100 | 100 | 100 | 100 | 100 | 100 | 100 |
| Atomization Gas Flow Rate (g/min) | 22 | 22 | 22 | 22 | 22 | 22 | 22 | 22 |
| Aqueous Flow (mL/min) | 8 | 16 | 24 | 32 | 8 | 16 | 24 | 32 |
| Organic flow (mL/min) | 32 | 24 | 16 | 8 | 32 | 24 | 16 | 8 |

TABLE 29-continued

| Lot Number | 117077 | 117078 | 117079 | 117080 | 117081 | 117082 | 117083 | 117084 |
|---|---|---|---|---|---|---|---|---|
| Secondary drying gas flow (kg/hr) | 0 | 0 | 0 | 0 | 0 | 0 | 0 | 0 |
| Secondary drying gas temperature (° C.) | 0 | 0 | 0 | 0 | 0 | 0 | 0 | 0 |
| Product filter purge gas flow (scfh) | 15 | 15 | 15 | 15 | 15 | 15 | 15 | 15 |
| Aqueous phase | Water | Water | Water | Water | Water | Water | Water | Water |
| Organic phase | Ethanol | Ethanol | Ethanol | Ethanol | Ethanol | Ethanol | Ethanol | Ethanol |
| Aircap | 67-6-20-150 | 67-6-20-150 | 67-6-20-150 | 67-6-20-150 | 67-6-20-150 | 67-6-20-150 | 67-6-20-150 | 67-6-20-150 |
| Fluid cap | 2850 | 2850 | 2850 | 2850 | 2850 | 2850 | 2850 | 2850 |

TABLE 30

| Lot Number | 117091 | 117092 | 117093 | 117094 |
|---|---|---|---|---|
| Total solid concentration (g/L) | 2 | 4 | 2 | 4 |
| Inlet Temperature (° C.) | 83 | 84.5 | 93 | 94 |
| Outlet Temperature (° C.) | 44 | 44 | 44 | 44 |
| Drying Gas Rate (kg/hr) | 100 | 100 | 100 | 100 |
| Atomization Gas Flow Rate (g/min) | 22 | 22 | 22 | 22 |
| Aqueous Flow (mL/min) | 16 | 16 | 24 | 24 |
| Organic flow (mL/min) | 24 | 24 | 16 | 16 |
| Secondary drying gas flow (kg/hr) | 50 | 50 | 50 | 50 |
| Secondary drying gas temperature (° C.) | 44 | 44 | 44 | 44 |
| Product filter purge gas flow (scfh) | 15 | 15 | 15 | 15 |
| Aqueous phase | Water | Water | Water | Water |
| Organic phase | Ethanol | Ethanol | Ethanol | Ethanol |
| Aircap | 67-6-20-150 | 67-6-20-150 | 67-6-20-150 | 67-6-20-150 |
| Fluid cap | 2850 | 2850 | 2850 | 2850 |

TABLE 31

| Lot Number | 117103 | 117104 | 117105 | 117106 |
|---|---|---|---|---|
| Total solid concentration (g/L) | 2 | 4 | 2 | 4 |
| Inlet Temperature (° C.) | 87 | 87 | 99 | 99 |
| Outlet Temperature (° C.) | 44 | 44 | 44 | 44 |
| Drying Gas Rate (kg/hr) | 100 | 100 | 100 | 100 |
| Atomization Gas Flow Rate (g/min) | 22 | 22 | 22 | 22 |
| Aqueous Flow (mL/min) | 16 | 16 | 24 | 24 |
| Organic flow (mL/min) | 24 | 24 | 16 | 16 |
| Secondary drying gas flow (kg/hr) | 50 | 50 | 50 | 50 |
| Secondary drying gas temperature (° C.) | 44 | 44 | 44 | 44 |
| Product filter purge gas flow (scfh) | 15 | 15 | 15 | 15 |
| Aqueous phase | Water | Water | Water | Water |
| Organic phase | Ethanol | Ethanol | Ethanol | Ethanol |
| Aircap | 67-6-20-150 | 67-6-20-150 | 67-6-20-150 | 67-6-20-150 |
| Fluid cap | 2850 | 2850 | 2850 | 2850 |

TABLE 32

| Lot Number | 117107 | 117108 | 117109 | 117110 |
|---|---|---|---|---|
| Total solid concentration (g/L) | 2 | 4 | 2 | 4 |
| Inlet Temperature (° C.) | 87 | 87 | 99 | 99 |
| Outlet Temperature (° C.) | 44 | 44 | 44 | 44 |
| Drying Gas Rate (kg/hr) | 100 | 100 | 100 | 100 |
| Atomization Gas Flow Rate (g/min) | 22 | 22 | 22 | 22 |
| Aqueous Flow (mL/min) | 16 | 16 | 24 | 24 |
| Organic flow (mL/min) | 24 | 24 | 16 | 16 |
| Secondary drying gas flow (kg/hr) | 50 | 50 | 50 | 50 |
| Secondary drying gas temperature (° C.) | 44 | 44 | 44 | 44 |
| Product filter purge gas flow (scfh) | 15 | 15 | 15 | 15 |
| Aqueous phase | Water | Water | Water | Water |
| Organic phase | Ethanol | Ethanol | Ethanol | Ethanol |
| Aircap | 67-6-20-150 | 67-6-20-150 | 67-6-20-150 | 67-6-20-150 |
| Fluid cap | 2850 | 2850 | 2850 | 2850 |

TABLE 33

| Lot Number | 117153-1 | 117153-2 | 117153-3 |
|---|---|---|---|
| Total solid concentration (g/L) | 4 | 4 | 4 |
| Inlet Temperature (° C.) | 78 | 78 | 78 |
| Outlet Temperature (° C.) | 44 | 44 | 44 |
| Drying Gas Rate (kg/hr) | 100 | 100 | 100 |
| Atomization Gas Flow Rate (g/min) | 22 | 33 | 44 |
| Aqueous Flow (mL/min) | 8 | 8 | 8 |
| Organic flow (mL/min) | 32 | 32 | 32 |
| Secondary drying gas flow (kg/hr) | 0 | 0 | 0 |
| Secondary drying gas temperature (° C.) | 0 | 0 | 0 |
| Product filter purge gas flow (scfh) | 15 | 15 | 15 |
| Aqueous phase | Water | Water | Water |
| Organic phase | Ethanol | Ethanol | Ethanol |
| Aircap | 67-6-20-150 | 67-6-20-150 | 67-6-20-150 |
| Fluid cap | 2850 | 2850 | 2850 |

TABLE 34

| Lot Number | 117177 | 117178 | 117179 | 117180 |
|---|---|---|---|---|
| Total solid concentration (g/L) | 4 | 4 | 4 | 4 |
| Inlet Temperature (° C.) | 78 | 78 | 78 | 78 |
| Outlet Temperature (° C.) | 44 | 44 | 44 | 44 |
| Drying Gas Rate (kg/hr) | 100 | 100 | 100 | 100 |
| Atomization Gas Flow Rate (g/min) | 44 | 44 | 44 | 44 |
| Aqueous Flow (mL/min) | 8 | 8 | 8 | 8 |
| Organic flow (mL/min) | 32 | 32 | 32 | 32 |
| Secondary drying gas flow (kg/hr) | 0 | 0 | 0 | 0 |
| Secondary drying gas temperature (° C.) | 0 | 0 | 0 | 0 |
| Product filter purge gas flow (scfh) | 15 | 15 | 15 | 15 |
| Aqueous phase | Water | Water | Water | Water |
| Organic phase | Ethanol | Ethanol | Ethanol | Ethanol |
| Aircap | 67-6-20-150 | 67-6-20-150 | 67-6-20-150 | 67-6-20-150 |
| Fluid cap | 2850 | 2850 | 2850 | 2850 |

TABLE 35

| Lot Number | 117186 | 117188 | 117190 | 117191 |
|---|---|---|---|---|
| Total solid concentration (g/L) | 6 | 6 | 6 | 6 |
| Inlet Temperature (° C.) | 86 | 87 | 86 | 87 |
| Outlet Temperature (° C.) | 44 | 44 | 44 | 44 |
| Drying Gas Rate (kg/hr) | 100 | 100 | 100 | 100 |
| Atomization Gas Flow Rate (g/min) | 44 | 44 | 44 | 44 |
| Aqueous Flow (mL/min) | 16 | 16 | 16 | 16 |
| Organic flow (mL/min) | 24 | 24 | 24 | 24 |
| Secondary drying gas flow (kg/hr) | 0 | 0 | 0 | 0 |
| Secondary drying gas temperature (° C.) | 0 | 0 | 0 | 0 |
| Product filter purge gas flow (scfh) | 15 | 15 | 15 | 15 |
| Aqueous phase | Water | Water | Water | Water |
| Organic phase | Ethanol | Ethanol | Ethanol | Ethanol |
| Aircap | 67-6-20-150 | 67-6-20-150 | 67-6-20-150 | 67-6-20-150 |
| Fluid cap | 2850 | 2850 | 2850 | 2850 |

TABLE 36

| Lot Number | 117164 | 117165 | 117166 | 117167 |
|---|---|---|---|---|
| Total solid concentration (g/L) | 6 | 6 | 6 | 6 |
| Inlet Temperature (° C.) | 89 | 89 | 89 | 89 |
| Outlet Temperature (° C.) | 44 | 44 | 44 | 44 |
| Drying Gas Rate (kg/hr) | 100 | 100 | 100 | 100 |
| Atomization Gas Flow Rate (g/min) | 44 | 44 | 44 | 44 |
| Aqueous Flow (mL/min) | 16 | 16 | 16 | 16 |
| Organic flow (mL/min) | 24 | 24 | 24 | 24 |
| Secondary drying gas flow (kg/hr) | 0 | 0 | 0 | 0 |
| Secondary drying gas temperature (° C.) | 0 | 0 | 0 | 0 |
| Product filter purge gas flow (scfh) | 15 | 15 | 15 | 15 |
| Aqueous phase | Water | Water | Water | Water |
| Organic phase | Ethanol | Ethanol | Ethanol | Ethanol |
| Aircap | 67147 | 67147 | 67147 | 67147 |
| Fluid cap | 2850 | 2850 | 2850 | 2850 |

TABLE 37

| Lot Number | 155039 | 155040 | 155034 | 155035 | 155036 | 155037 | 155038 |
|---|---|---|---|---|---|---|---|
| Total solid concentration (g/L) | 4 | 4 | 4 | 4 | 4 | 4 | 4 |
| Inlet Temperature (° C.) | 79 | 79 | 79 | 79 | 79 | 79 | 79 |
| Outlet Temperature (° C.) | 44 | 44 | 44 | 44 | 44 | 44 | 44 |
| Drying Gas Rate (kg/hr) | 100 | 100 | 100 | 100 | 100 | 100 | 100 |
| Atomization Gas Flow Rate (g/min) | 33 | 33 | 33 | 33 | 33 | 33 | 33 |
| Aqueous Flow (mL/min) | 8 | 8 | 8 | 8 | 8 | 8 | 8 |
| Organic flow (mL/min) | 32 | 32 | 32 | 32 | 32 | 32 | 32 |
| Secondary drying gas flow (kg/hr) | 0 | 0 | 0 | 0 | 0 | 0 | 0 |
| Secondary drying gas temperature (° C.) | 0 | 0 | 0 | 0 | 0 | 0 | 0 |
| Product filter purge gas flow (scfh) | 15 | 15 | 15 | 15 | 15 | 15 | 15 |
| Aqueous phase | Water | Water | Water | Water | Water | Water | Water |
| Organic phase | Ethanol | Ethanol | Ethanol | Ethanol | Ethanol | Ethanol | Ethanol |
| Aircap | 67-6-20-150 | | | | | | |
| Fluid cap | 2850 | | | | | | |

TABLE 38

| Lot Number | 155046 | 155047 | 155048 | 155049 |
|---|---|---|---|---|
| Total solid concentration (g/L) | 4 | 4 | 4 | 4 |
| Inlet Temperature (° C.) | 81 | 100 | 81 | 100 |
| Outlet Temperature (° C.) | 44 | 60 | 44 | 60 |
| Drying Gas Rate (kg/hr) | 100 | 100 | 100 | 100 |
| Atomization Gas Flow Rate (g/min) | 22 | 22 | 22 | 22 |
| Aqueous Flow (mL/min) | 8 | 8 | 8 | 8 |
| Organic flow (mL/min) | 32 | 32 | 32 | 32 |
| Secondary drying gas flow (kg/hr) | 0 | 0 | 0 | 0 |
| Secondary drying gas temperature (° C.) | 0 | 0 | 0 | 0 |
| Product filter purge gas flow (scfh) | 15 | 15 | 15 | 15 |
| Aqueous phase | Water | Water | Water | Water |
| Organic phase | Ethanol | Ethanol | Ethanol | Ethanol |
| Aircap | 67-6-20-150 | 67-6-20-150 | 67-6-20-150 | 67-6-20-150 |
| Fluid cap | 2850 | 2850 | 2850 | 2850 |

TABLE 39

| | |
|---|---|
| Total solid concentration (g/L) | 4 |
| Inlet Temperature (° C.) | 79 |
| Outlet Temperature (° C.) | 44 |
| Drying Gas Rate (kg/hr) | 100 |
| Atomization Gas Flow Rate (g/min) | 22 |
| Aqueous Flow (mL/min) | 8 |
| Organic flow (mL/min) | 32 |
| Secondary drying gas flow (kg/hr) | 0 |
| Secondary drying gas temperature (° C.) | 0 |
| Product filter purge gas flow (scfh) | 15 |
| Aqueous phase | Water |
| Organic phase | Ethanol |
| Aircap | 67-6-20-150 |
| Fluid cap | 2850 |

TABLE 40

| | |
|---|---|
| Total solid concentration (g/L) | 4 |
| Inlet Temperature (° C.) | 79 |
| Outlet Temperature (° C.) | 44 |
| Drying Gas Rate (kg/hr) | 100 |
| Atomization Gas Flow Rate (g/min) | 22 |
| Aqueous Flow (mL/min) | 8 |
| Organic flow (mL/min) | 32 |
| Secondary drying gas flow (kg/hr) | 0 |
| Secondary drying gas temperature (° C.) | 0 |
| Product filter purge gas flow (scfh) | 15 |
| Aqueous phase | Water |
| Organic phase | Ethanol |
| Aircap | 67-6-20-150 |
| Fluid cap | 2850 |

TABLE 41

| Lot Number | 155043 | 155044 | 155041 | 155042 |
|---|---|---|---|---|
| Total solid concentration (g/L) | 4 | 4 | 4 | 4 |
| Inlet Temperature (° C.) | 87 | 87 | 87 | 87 |
| Outlet Temperature (° C.) | 50 | 50 | 50 | 50 |
| Drying Gas Rate (kg/hr) | 100 | 100 | 100 | 100 |
| Atomization Gas Flow Rate (g/min) | 33 | 33 | 33 | 33 |
| Aqueous Flow (mL/min) | 8 | 8 | 8 | 8 |
| Organic flow (mL/min) | 32 | 32 | 32 | 32 |
| Secondary drying gas flow (kg/hr) | 0 | 0 | 0 | 0 |
| Secondary drying gas temperature (° C.) | 0 | 0 | 0 | 0 |
| Product filter purge gas flow (scfh) | 15 | 15 | 15 | 15 |
| Aqueous phase | Water | Water | Water | Water |
| Organic phase | Ethanol | Ethanol | Ethanol | Ethanol |
| Aircap | 67-6-20-150 | 67-6-20-150 | 67-6-20-150 | 67-6-20-150 |
| Fluid cap | 2850 | 2850 | 2850 | 2850 |

TABLE 42

| Lot Number | 155059 | 155060 | 155061 | 155062 | 155063 | 155064 | 155065 |
|---|---|---|---|---|---|---|---|
| Total solid concentration (g/L) | 4 | 4 | 4 | 4 | 4 | 4 | 4 |
| Inlet Temperature (° C.) | 120 | 120 | 120 | 120 | 120 | 120 | 120 |
| Outlet Temperature (° C.) | 60 | 60 | 60 | 60 | 60 | 60 | 60 |
| Drying Gas Rate (kg/hr) | 100 | 100 | 100 | 100 | 100 | 100 | 100 |
| Atomization Gas Flow Rate (g/min) | 44 | 44 | 44 | 44 | 44 | 44 | 44 |
| Aqueous Flow (mL/min) | 12 | 12 | 12 | 12 | 12 | 12 | 12 |
| Organic flow (mL/min) | 48 | 48 | 48 | 48 | 48 | 48 | 48 |
| Secondary drying gas flow (kg/hr) | 0 | 0 | 0 | 0 | 0 | 0 | 0 |
| Secondary drying gas temperature (° C.) | 0 | 0 | 0 | 0 | 0 | 0 | 0 |

TABLE 42-continued

| Lot Number | 155059 | 155060 | 155061 | 155062 | 155063 | 155064 | 155065 |
|---|---|---|---|---|---|---|---|
| Product filter purge gas flow (scfh) | 15 | 15 | 15 | 15 | 15 | 15 | 15 |
| Aqueous phase | Water | Water | Water | Water | Water | Water | Water |
| Organic phase | Ethanol | Ethanol | Ethanol | Ethanol | Ethanol | Ethanol | Ethanol |
| Aircap | 67-6-20-150 | 67-6-20-150 | 67-6-20-150 | 67-6-20-150 | 67-6-20-150 | 67-6-20-150 | 67-6-20-150 |
| Fluid cap | 2850 | 2850 | 2850 | 2850 | 2850 | 2850 | 2850 |

TABLE 43

| Lot Number | 155091 | 155092 | 155094 | 155095 | 155097 | 155098 | 155100-1 | 155100-2 |
|---|---|---|---|---|---|---|---|---|
| Total solid concentration (g/L) | 4 | 4 | 4 | 4 | 4 | 4 | 4 | 4 |
| Inlet Temperature (° C.) | 79 | 79 | 79 | 79 | 79 | 79 | 79 | 79 |
| Outlet Temperature (° C.) | 44 | 44 | 44 | 44 | 44 | 44 | 44 | 44 |
| Drying Gas Rate (kg/hr) | 100 | 100 | 100 | 100 | 100 | 100 | 100 | 100 |
| Atomization Gas Flow Rate (g/min) | 33 | 33 | 33 | 33 | 33 | 33 | 33 | 33 |
| Aqueous Flow (mL/min) | 8 | 8 | 8 | 8 | 8 | 8 | 8 | 8 |
| Organic flow (mL/min) | 32 | 32 | 32 | 32 | 32 | 32 | 32 | 32 |
| Secondary drying gas flow (kg/hr) | 0 | 0 | 0 | 0 | 0 | 0 | 0 | 0 |
| Secondary drying gas temperature (° C.) | 0 | 0 | 0 | 0 | 0 | 0 | 0 | 0 |
| Product filter purge gas flow (scfh) | 15 | 15 | 15 | 15 | 15 | 15 | 15 | 15 |
| Aqueous phase | Water | Water | Water | Water | Water | Water | Water | Water |
| Organic phase | Ethanol | Ethanol | Ethanol | Ethanol | Ethanol | Ethanol | Ethanol | Ethanol |
| Aircap | 67-6-20-150 | 67-6-20-150 | 67-6-20-150 | 67-6-20-150 | 67-6-20-150 | 67-6-20-150 | 67-6-20-150 | 67-6-20-150 |
| Fluid cap | 2850 | 2850 | 2850 | 2850 | 2850 | 2850 | 2850 | 2850 |

TABLE 44

| Lot Number | 155104 | 155105 | 155106 | 155107 | 155108 |
|---|---|---|---|---|---|
| Total solid concentration (g/L) | 4 | 4 | 4 | 4 | 4 |
| Inlet Temperature (° C.) | 103 | 103 | 103 | 103 | 103 |
| Outlet Temperature (° C.) | 60 | 60 | 60 | 60 | 60 |
| Drying Gas Rate (kg/hr) | 100 | 100 | 100 | 100 | 100 |
| Atomization Gas Flow Rate (g/min) | 33 | 33 | 33 | 33 | 33 |
| Aqueous Flow (mL/min) | 8 | 8 | 8 | 8 | 8 |
| Organic flow (mL/min) | 32 | 32 | 32 | 32 | 32 |
| Secondary drying gas flow (kg/hr) | 0 | 0 | 0 | 0 | 0 |
| Secondary drying gas temperature (° C.) | 0 | 0 | 0 | 0 | 0 |
| Product filter purge gas flow (scfh) | 15 | 15 | 15 | 15 | 15 |
| Aqueous phase | Water | Water | Water | Water | Water |

TABLE 44-continued

| Organic phase | Ethanol | Ethanol | Ethanol | Ethanol | Ethanol | | |
|---|---|---|---|---|---|---|---|
| Lot Number | 155109 | 155110 | 155111 | 155112 | 155113 | 155114 | 155115 |
| Total solid concentration (g/L) | 4 | 4 | 4 | 4 | 4 | 4 | 4 |
| Inlet Temperature (° C.) | 103 | 103 | 103 | 103 | 103 | 117 | 125 |
| Outlet Temperature (° C.) | 60 | 60 | 60 | 60 | 60 | 60 | 60 |
| Drying Gas Rate (kg/hr) | 100 | 100 | 100 | 100 | 100 | 100 | 100 |
| Atomization Gas Flow Rate (g/min) | 33 | 33 | 33 | 33 | 33 | 33 | 33 |
| Aqueous Flow (mL/min) | 8 | 8 | 8 | 8 | 8 | 12 | 16 |
| Organic flow (mL/min) | 32 | 32 | 32 | 32 | 32 | 48 | 64 |
| Secondary drying gas flow (kg/hr) | 0 | 0 | 0 | 0 | 0 | 0 | 0 |
| Secondary drying gas temperature (° C.) | 0 | 0 | 0 | 0 | 0 | 0 | 0 |
| Product filter purge gas flow (scfh) | 15 | 15 | 15 | 15 | 15 | 15 | 15 |
| Aqueous phase | Water | Water | Water | Water | Water | Water | Water |
| Organic phase | Ethanol | Ethanol | Ethanol | Ethanol | Ethanol | Ethanol | Ethanol |

TABLE 45

| Lot Number | 155125 | 155126 | 155127 | 155128 | 155129 |
|---|---|---|---|---|---|
| Total solid concentration (g/L) | 4 | 4 | 4 | 4 | 4 |
| Inlet Temperature (° C.) | 103 | 103 | 103 | 103 | 103 |
| Outlet Temperature (° C.) | 60 | 60 | 60 | 60 | 60 |
| Drying Gas Rate (kg/hr) | 100 | 100 | 100 | 100 | 100 |
| Atomization Gas Flow Rate (g/min) | 33 | 33 | 33 | 33 | 33 |
| Aqueous Flow (mL/min) | 8 | 8 | 8 | 8 | 8 |
| Organic flow (mL/min) | 32 | 32 | 32 | 32 | 32 |
| Secondary drying gas flow (kg/hr) | 0 | 0 | 0 | 0 | 0 |
| Secondary drying gas temperature (° C.) | 0 | 0 | 0 | 0 | 0 |
| Product filter purge gas flow (scfh) | 15 | 15 | 15 | 15 | 15 |
| Aqueous phase | Water | Water | Water | Water | Water |
| Organic phase | Ethanol | Ethanol | Ethanol | Ethanol | Ethanol |
| Aircap | 67-6-20-150 | 67-6-20-150 | 67-6-20-150 | 67-6-20-150 | 67-6-20-150 |
| Fluid cap | 2850 | 2850 | 2850 | 2850 | 2850 |
| Lot Number | 155130 | 155131 | 155132 | 155133 | 155134 |
| Total solid concentration (g/L) | 4 | 4 | 4 | 4 | 4 |
| Inlet Temperature (° C.) | 103 | 103 | 103 | 103 | 103 |
| Outlet Temperature (° C.) | 60 | 60 | 60 | 60 | 60 |
| Drying Gas Rate (kg/hr) | 100 | 100 | 100 | 100 | 100 |
| Atomization Gas Flow Rate (g/min) | 33 | 33 | 33 | 33 | 33 |
| Aqueous Flow (mL/min) | 8 | 8 | 8 | 8 | 8 |
| Organic flow (mL/min) | 32 | 32 | 32 | 32 | 32 |
| Secondary drying gas flow (kg/hr) | 0 | 0 | 0 | 0 | 0 |

TABLE 45-continued

| | | | | | |
|---|---|---|---|---|---|
| Secondary drying gas temperature (° C.) | 0 | 0 | 0 | 0 | 0 |
| Product filter purge gas flow (scfh) | 15 | 15 | 15 | 15 | 15 |
| Aqueous phase | Water | Water | Water | Water | Water |
| Organic phase | Ethanol | Ethanol | Ethanol | Ethanol | Ethanol |
| Aircap | 67-6-20-150 | 67-6-20-150 | 67-6-20-150 | 67-6-20-150 | 67-6-20-150 |
| Fluid cap | 2850 | 2850 | 2850 | 2850 | 2850 |

TABLE 46

| | | 189065-1 | 189065-2 | 189065-3 |
|---|---|---|---|---|
| Parameters | Total solid concentration (g/L) | 4 | 4 | 4 |
| | Inlet Temperature (° C.) | 78 | 87 | 103 |
| | Outlet Temperature (° C.) | 40 | 50 | 60 |
| | Drying Gas Rate (kg/hr) | 100 | 100 | 100 |
| | Atomization Gas Flow Rate (g/min) | 22 | 22 | 22 |
| | Aqueous Flow (mL/min) | 8 | 8 | 8 |
| | Organic flow (mL/min) | 32 | 32 | 32 |
| | Secondary drying gas flow (kg/hr) | 0 | 0 | 0 |
| | Secondary drying gas temperature (° C.) | 0 | 0 | 0 |
| | Product filter purge gas flow (scfh) | 15 | 15 | 15 |
| Atomization nozzle | Air cap | 67-6-20-150 | 67-6-20-150 | 67-6-20-150 |
| | Fluid cap | 2850 | 2850 | 2850 |

TABLE 47

| | | Value |
|---|---|---|
| Parameters | Total solid concentration (g/L) | 4 |
| | Inlet Temperature (° C.) | 103 |
| | Outlet Temperature (° C.) | 60 |
| | Drying Gas Rate (kg/hr) | 100 |
| | Atomization Gas Flow Rate (g/min) | 22 |
| | Aqueous Flow (mL/min) | 8 |
| | Organic flow (mL/min) | 32 |
| | Secondary drying gas flow (kg/hr) | 0 |
| | Secondary drying gas temperature (° C.) | 0 |
| | Product filter purge gas flow (scfh) | 15 |
| Atomization nozzle | Air cap | 67-6-20-150 |
| | Fluid cap | 2850 |

TABLE 48

| | | Value |
|---|---|---|
| Parameters | Total solid concentration (g/L) | 4 |
| | Inlet Temperature (° C.) | 103 |
| | Outlet Temperature (° C.) | 60 |
| | Drying Gas Rate (kg/hr) | 100 |
| | Atomization Gas Flow Rate (g/min) | 22 |
| | Aqueous Flow (mL/min) | 16 |
| | Organic flow (mL/min) | 24 |
| | Secondary drying gas flow (kg/hr) | 0 |
| | Secondary drying gas temperature (° C.) | 0 |
| | Product filter purge gas flow (scfh) | 15 |
| Atomization nozzle | Air cap | 67147 |
| | Fluid cap | 2850 |

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A pharmaceutical composition for pulmonary delivery to the respiratory tract of a patient comprising spray-dried particles comprising a triptan or a pharmaceutically salt thereof and a phospholipid, wherein the triptan or salt thereof is present in the particles (a) in crystalline form or (b) in both crystalline and amorphous forms.

2. The pharmaceutical composition of claim 1, wherein the triptan is sumatriptan or a pharmaceutically acceptable salt thereof.

3. The pharmaceutical composition of claim 2, wherein the triptan is sumatriptan succinate.

4. The pharmaceutical composition of claim 1, wherein the triptan is sumatriptan free base.

5. The pharmaceutical composition of claim 1, wherein the spray-dried particles further comprise a salt, an amino acid or a sugar.

6. The pharmaceutical composition of claim 1, wherein the particles comprise sumatriptan or a pharmaceutically acceptable salt thereof in crystalline form.

7. The pharmaceutical composition of claim 1, wherein the particles comprise sumatriptan or a pharmaceutically acceptable salt thereof in both crystalline and amorphous forms.

8. The pharmaceutical composition of claim 1, wherein the particles comprise sumatriptan or a pharmaceutically acceptable salt thereof, DPPC, sodium chloride and maltodextrin.

9. The pharmaceutical composition of claim 1, wherein the particles comprise sumatriptan or a pharmaceutically acceptable salt thereof, DPPC, sodium chloride and l-leucine.

10. The pharmaceutical composition of claim 1, wherein the particles comprise 5 to 50% triptan or a pharmaceutically acceptable salt thereof, 5-20% phospholipid, and 1-10% sodium chloride as measured by percent of dry solids in the powder.

11. The pharmaceutical composition of claim 1, wherein the particles comprise 25 to 55% triptan or a pharmaceutically acceptable salt thereof, 5-20% phospholipid, 1-10% sodium chloride and 25 to 60% of an excipient selected from maltodextrins, lactose, glycine, trehalose, mannitol and l-leucine, as measured by percent of dry solids in the powder.

12. The pharmaceutical composition of claim 11, wherein the triptan is sumatriptan free base or a sumatriptan salt.

13. The pharmaceutical composition of claim 12, wherein the particles comprise 25 to 55% sumatriptan free base, 15-20% phospholipid, 1-5% sodium chloride and 25 to 55% of an excipient selected from maltodextrins, and l-leucine, as measured by percent of dry solids.

14. The pharmaceutical composition of claim 13, wherein the particles comprise 30 to 50% sumatriptan free base, about 18% phospholipid, about 2% sodium chloride and 30 to 50% of an excipient selected from maltodextrins or l-leucine as measured by percent of dry solids.

15. The pharmaceutical composition of claim 14, wherein the phospholipid is DPPC.

16. The pharmaceutical composition of claim 14 wherein the maltodextrin is (i) maltodextrin with D.E.=10.7 or (ii) SD-30.

17. The pharmaceutical composition of claim 14 comprising l-leucine.

18. A powder formulation for pulmonary delivery to the respiratory tract of a patient, said powder comprising particles having a composition selected from the table below, as measured by weight percent of dry solids in the powder:

| Sumatriptan Succinate | DPPC | Sodium Chloride | l-leucine | Sugar/Sugar alcohol |
|---|---|---|---|---|
| 25% | 18% | 2% | 55% | 0 |
| 50% | 18% | 2% | 30% | 0 |
| 50% | 18% | 2% | 0 | 30% maltodextrin |
| 50% | 18% | 2% | 0 | 30% lactose |
| 50% | 18% | 2% | 0 | 30% mannitol |
| 50% | 18% | 2% | 0 | 30% trehalose |
| 25% | 18% | 2% | 0 | 55% trehalose | wherein the sumatriptan succinate is present (a) in crystalline form or (b) both crystalline and amorphous forms.

19. A powder formulation for pulmonary delivery to the respiratory tract of a patient, said powder comprising particles having a composition selected from the table below, as measured by weight percent of dry solids in the powder:

| Sumatriptan Free base | DPPC | Sodium Chloride | Amino Acid | Sugar/Sugar alcohol |
|---|---|---|---|---|
| 50% | 18% | 2% | 30% leucine | 0 |
| 50% | 18% | 2% | 0 | 30% maltodextrin |
| 50% | 18% | 2% | 0 | 30% lactose |
| 50% | 18% | 2% | 30% glycine | 0 | wherein the sumatriptan free base is present (a) in crystalline form or (b) both crystalline and amorphous forms.

20. A method of delivering sumatriptan or a salt thereof to the pulmonary system of a patient comprising the steps of: a) providing a pharmaceutical composition of claim 1 in a compartment and an inhaler to a patient; b) dispersing the particles by breath actuation of the patient; and c) delivering the particles to the patient's respiratory system.

21. A method of treating migraine in a subject in need thereof, comprising administering to the pulmonary system of the subject a therapeutically effective amount of the pharmaceutical composition of claim 1.

22. A method of treating cluster headache in a subject in need thereof, comprising administering to the pulmonary system of the subject a therapeutically effective amount of the powder formulation of claim 1.

* * * * *